US010344291B2

(12) United States Patent
Hunter et al.

(10) Patent No.: US 10,344,291 B2
(45) Date of Patent: Jul. 9, 2019

(54) DOUBLE STRANDED RNA COMPOSITIONS FOR REDUCING ASIAN CITRUS PSYLLID INFESTATION AND METHODS OF USE

(71) Applicants: The United States of America, as represented by the Secretary of Agriculture, Washington, DC (US); Embrapa, PqEB Parque Estacao Biologica, Plano Piloto-Brasilia (BR)

(72) Inventors: Wayne B. Hunter, Port St. Lucie, FL (US); Maria T. Gonzalez, Port St. Lucie, FL (US); Eduardo C. Andrade, Cruz das Almas (BR)

(73) Assignees: The United States of America, as Represented by the Secretary of Agriculture, Washington, DC (US); Empresa Brasileira De Pesquisa Agropecuaria, Brasilia, DF (BR)

( * ) Notice: Subject to any disclaimer, the term of this patent is extended or adjusted under 35 U.S.C. 154(b) by 0 days.

(21) Appl. No.: 15/414,800

(22) Filed: Jan. 25, 2017

(65) Prior Publication Data
US 2017/0211082 A1 Jul. 27, 2017

Related U.S. Application Data

(60) Provisional application No. 62/287,315, filed on Jan. 26, 2016.

(51) Int. Cl.
*C12N 15/82* (2006.01)
*C12N 9/24* (2006.01)
*C12N 7/00* (2006.01)
*A01N 57/16* (2006.01)
*A01N 25/08* (2006.01)

(52) U.S. Cl.
CPC ......... *C12N 15/8218* (2013.01); *A01N 25/08* (2013.01); *A01N 57/16* (2013.01); *C12N 7/00* (2013.01); *C12N 9/2402* (2013.01); *C12N 15/8286* (2013.01); *C12Y 302/01028* (2013.01); *C12N 2700/00* (2013.01)

(58) Field of Classification Search
CPC .................................................. C12N 15/8218
USPC .................................................. 800/279, 285
See application file for complete search history.

(56) References Cited

U.S. PATENT DOCUMENTS

| 7,968,525 | B1 | 6/2011 | Scharf et al. |
| 8,759,306 | B2 | 6/2014 | Kaletta |
| 8,772,572 | B2 | 7/2014 | Niblett |
| 8,853,489 | B2 | 10/2014 | Raemaekers et al. |
| 8,877,727 | B2 | 11/2014 | Whyard et al. |
| 8,895,721 | B2 | 11/2014 | Tuschl et al. |
| 2010/0257634 | A1 | 10/2010 | Bailey et al. |
| 2011/0296556 | A1 | 12/2011 | Sammons et al. |
| 2013/0125254 | A1 | 5/2013 | Dawson et al. |
| 2013/0125256 | A1 | 5/2013 | Bailey et al. |
| 2013/0305417 | A1 | 11/2013 | Vander Meer et al. |
| 2015/0067918 | A1 | 3/2015 | Kress |

FOREIGN PATENT DOCUMENTS

EP 2730657 A1 9/2010

OTHER PUBLICATIONS

Thomas et al. 2001, The Plant Journal 25(4):417-425.*
Evans, Jay D., Protocol and budget for real-time PCR diagnostics for honey bees; (2006); Beepath: An ordered quantitative-PCR array for exploring honey bee immunity.
Barrangou, Rodolphe et al., Survey and Summary Advances in CRISPR-Cas9 genome engineering: lessons learned from RNA interference; Nucleic Acids Research, (2015), 43(7): 3407-3419.
Bassett, Andrew R. et al., CRISPR/Cas9 and Genome Editing in *Drosophila*\*, Journal of Genetics and Genomics, (2014), 41: 7-19.
Beane, Randall L. et al., Inhibiting Gene Expression with Locked Nucleic Acids (LNAs) that Target Chromosomal DNA, Biochemistry, (2007), 46(25):7572-7580.
Chen, Changchun et al., Efficient genome editing in Caenorhabditis elegans by CRISPR-targeted homologous recombination; Nucleic Acids Research, (2013), 41(20): 193.
Evans, J.D. et al., Immune pathways and defence mechanisms in honey bees Apis mellifera; Insect Molecular Biology, (2006), 15(5): 645-656.
Guleria, Praveen et al., Plant Small RNAs: Biogenesis, Mode of Action and Their Roles in Abiotic Stresses; Genomics Proteomics Bioinformatics, (2011); 9(9): 183-199.
Hall, David G. et al., Asian citrus psyllid, Diaphorina citri, vector of citrus huanglongbing disease; The Authors Entomologia Experimentalis et Applicata, (2012), 146: 207-223.
Hamilton, Andrew et al., Two classes of short interfering RNA in RNA silencing; The EMRO Journal, (2002), 21 (17):4671-4679.
Li, Jie et al., Advances in the use of the RNA interference technique in Hemiptera; Insect Science, (2013), 20:31-39.
Reese, Justin et al., Characterization of the Asian Citrus Psyllid Transcriptome; Journal of Genomics, (2013), 2:54-58.
Shultz, Sharon J. et al., RNase H Activity: Structure, Specificity, and Function in Reverse Transcription; Virus Res., (2008); 134(1-2): 86-103.
Wesolowski, Donna et al., Combined effect of a peptide-morpholino oligonucleotide conjugate and a cell-penetrating peptide as an antibiotic, PNAS, (2013), 110(21):8686-8689.

\* cited by examiner

*Primary Examiner* — Li Zheng
(74) *Attorney, Agent, or Firm* — John Fado; Maria Restrepo-Hartwig

(57) ABSTRACT dsRNA generated from *D. citri* trehalase gene is effective in reducing fitness and/or survival of *D. citri*. Thus genetically altered plants expressing the dsRNA and plants to which dsRNA solutions are applied increase *D. citri* mortality and reduce *D. citri* infestation. With reduced *D. citri* population, the spread of microorganisms for which *D. citri* is a vector is reduced. Such microorganisms include, but are not limited to, *C. Liberibacter* species, including: CLas, CLam, and CLaf. Thus, applying of the *D. citri* trehalase dsRNA to a plant reduces disease and/or microorganism transmission by killing *D. citri* that feed on the treated plant.

38 Claims, 1 Drawing Sheet
Specification includes a Sequence Listing.

FIG. 1

AGTATACGGCGACACCAACTTTATAAGAACCCACCTTAAGTCACTAACCAACGAGTTTGAATACTGGAT
GAAGAGACATATGGTCACTGTAGAGAAAAATGGCAAGTACTACACCATGGCTCGATACTACGCTCCGTCC
AGAGGCCCTAGGCCCGAGTCTTACAGAGAGGACTACCATGAGGCAGCAGATTTGCAGACAGAGGATGAGA
AAAACTTCCTGTACTCAGAGCTGAAGGCAGGTGCCGAAACCGGATGGGACTTTTCCAGTCGGTGGTTCAT
CGCACGGGACGGTAGCAATAGAGGAGGCCTCAAATACATTCGCACCACATCGATCATTCCCGTGGACCTC
AATGCGATCCTTCAGATGAACGCTAACTATCTGAGCGAATGGTGGCTCAAATTTGGCAACAAGGATTTGA
GTGCCAAGTACAAGAAGATTGCGTACCAACTGCTTGAAGCCATTCATGA (SEQ ID NO: 1)

FIG. 2

TGAGCTGAGGACGATTGATGATTTCAGCCAAATCTACTGCAAGGGAGAACTTCTGGACAAGGTACAGCGA
GGAAACGTGTTTCCAAACGACTCGAAATCGTTTGTCGATCTCAAACTGAAACAGCCAGAGGACGTGATTC
TGGCCAAGTTCCGAGCCTTGCTCACCAATAATGCTGATCCCGACACCACCACACTGACCAACTTTGTCAA
CGAATACTTTGAAGCAGGCAATGAGCTGCAAGTCTGGAGTCCTCCAGATTTCACCTCCAACCCGAGTATC
GAGAACAAAATCTCCGACGCCAAATACAGACAGTTTGCCCTCGACCTGAACCAAATTTGGAAAGAGTTGG
GCCGCATAGTAAAACAAGATGTAAGGGACAACCCTCAACTGTACTCACTCATATACACACCCAATGGA**TT
CTTCATTCCTGGAGGACG**    (SEQ ID NO: 6)

FIG. 3

TCAATGCGATCCTTCAGATGAACGCTAACTATCTGAGCGAATGGTGGCTCAAATTTGGCAACAAGGATTT
GAGTGCCAAGTACAAGAAGATTGCGTACCAACTGCTTGAAGCCATTCATGAGGTTCTATGGAATGAACAG
GTTGGTGTATGGCTAGACTACGACATTAAGAACAAGAAGCCCCGAAATTATTTCTACGTCTCAAACATAA
CTCCTCTGTGGACATTGAGCTACAAATTCTCCAAACAATATGTGGCTGAGAGAGTACTGCAGTATTTGCG
AGACAATGAAATCATCACCAAGGACAATCAAGTGAAATTCTATGGTACCCCTACCTCCTTGTTCAACTCT
ACTCAACAATGGGATTACCCTAATGCCTGGGCCCACTACAGGCATTCATCATACAAGGCTTGGACTACA
CGCAAGACAAATTAGCAAAGCAAGTGGCATACCGACTGGCTGAAAAGTGGCTCTTCACAAACTATATGGG
CTATGAAACTAGCAAGGCTATGTTTGAGAAATATGATGTAGAACTCATTGGAAAGACAGGTAATGGAGGT
GAGTACGAGGCACAAACTGGATTTGGTTGGACCAATGGATTCGCATTTGAGCTTCTAAATAGATACGGAA
AAACTATATCTTTCAACAATACTCAAGGAAGCTACTACAATAAAATCCCCGGATCCGGTTACTTATCCGG
CTATTATCCGTCTTTCATGTCCGGAAGACC    (SEQ ID NO: 11)

SEQUENCE LISTING

```
<160> NUMBER OF SEQ ID NOS: 29

<210> SEQ ID NO 1
<211> LENGTH: 469
<212> TYPE: DNA
<213> ORGANISM: Diaphornia citri

<400> SEQUENCE: 1
agtatacggg cgacaccaac tttataagaa cccaccttaa gtcactaacc aacgagtttg      60
aatactggat gaagagacat atggtcactg tagagaaaaa tggcaagtac tacaccatgg     120
ctcgatacta cgctccgtcc agaggcccta ggcccgagtc ttacagagag gactaccatg     180
aggcagcaga tttgcagaca gaggatgaga aaaacttcct gtactcagag ctgaaggcag     240
gtgccgaaac cggatgggac ttttccagtc ggtggttcat cgcacgggac ggtagcaata     300
gaggaggcct caaatacatt cgcaccacat cgatcattcc cgtggacctc aatgcgatcc     360
ttcagatgaa cgctaactat ctgagcgaat ggtggctcaa atttggcaac aaggatttga     420
gtgccaagta caagaagatt gcgtaccaac tgcttgaagc cattcatga                 469

<210> SEQ ID NO 2
<211> LENGTH: 42
<212> TYPE: DNA
<213> ORGANISM: Artificial Sequence
<220> FEATURE:
<223> OTHER INFORMATION: Primer

<400> SEQUENCE: 2
taatacgact cactataggg agagtatacg ggcgacacca ac                         42

<210> SEQ ID NO 3
<211> LENGTH: 42
<212> TYPE: DNA
<213> ORGANISM: Artificial Sequence
<220> FEATURE:
<223> OTHER INFORMATION: Primer

<400> SEQUENCE: 3
```

-continued taatacgact cactataggg agtcatgaat ggcttcaagc ag 42

<210> SEQ ID NO 4
<211> LENGTH: 469
<212> TYPE: RNA
<213> ORGANISM: Diaphornia citri

<400> SEQUENCE: 4
aguauacggg cgacaccaac uuuauaagaa cccaccuuaa gucacuaacc aacgaguuug 60
aauacuggau gaagagacau auggucacug uagagaaaaa uggcaaguac uacaccaugg 120
cucgauacua cgcuccgucc agaggcccua ggcccgaguc uuacagagag gacuaccaug 180
aggcagcaga uuugcagaca gaggaugaga aaaacuuccu guacucagag cugaaggcag 240
gugccgaaac cggaugggac uuuuccaguc ggugguucau cgcacgggac gguagcaaua 300
gaggaggccu caaauacauu cgcaccacau cgaucauucc cguggaccuc aaugcgaucc 360
uucagaugaa cgcuaacuau cugagcgaau gguggcucaa auuuggcaac aaggauuuga 420
gugccaagua caagaagauu gcguaccaac ugcuugaagc cauucauga 469

<210> SEQ ID NO 5
<211> LENGTH: 469
<212> TYPE: RNA
<213> ORGANISM: Diaphornia citri

<400> SEQUENCE: 5
ucauaugccc gcugugguug aaauauucuu ggguggaauu cagugauugg uugcucaaac 60
uuaugaccua cuucucugua uaccagugac aucucuuuuu accguucaug augugguacc 120
gagcuaugau gcgaggcagg ucuccgggau ccgggcucag aaugucucuc cugaugguac 180
uccgucgucu aaacgucugu cuccuacucu uuuugaagga caugagucuc gacuuccguc 240
cacggcuuug gccuacccug aaaaggucag ccaccaagua gcgugcccug ccaucguuau 300
cuccuccgga guuuauguaa gcguggugua gcuaguaagg gcaccuggag uuacgcuagg 360
aagucuacuu gcgauugaua gacucgcuua ccaccgaguu uaaaccguug uuccuaaacu 420
cacgguucau guucuucuaa cgcaugguug acgaacuucg guaaguacu 469

<210> SEQ ID NO 6
<211> LENGTH: 438
<212> TYPE: DNA
<213> ORGANISM: Diaphornia citri

<400> SEQUENCE: 6
tgagctgagg acgattgatg atttcagcca aatctactgc aagggagaac ttctggacaa 60
ggtacagcga ggaaacgtgt ttccaaacga ctcgaaatcg tttgtcgatc tcaaactgaa 120
acagccagag gacgtgattc tggccaagtt ccgagccttg ctcaccaata atgctgatcc 180
cgacaccacc acactgacca actttgtcaa cgaatacttt gaagcaggca atgagctgca 240
agtctggagt cctccagatt tcacctccaa cccgagtatc gagaacaaaa tctccgacgc 300
caaatacaga cagtttgccc tcgacctgaa ccaaatttgg aaagagttgg gccgcatagt 360
aaaacaagat gtaaggacaa accctcaact gtactcactc atatacacac ccaatggatt 420
cttcattcct ggaggacg 438

<210> SEQ ID NO 7
<211> LENGTH: 42
<212> TYPE: DNA

<210> SEQ ID NO 7
<211> LENGTH: 42
<212> TYPE: DNA
<213> ORGANISM: Artificial Sequence
<220> FEATURE:
<223> OTHER INFORMATION: Primer

<400> SEQUENCE: 7
taatacgact cactataggg agtgagctga ggacgattga tg          42

<210> SEQ ID NO 8
<211> LENGTH: 42
<212> TYPE: DNA
<213> ORGANISM: Artificial Sequence
<220> FEATURE:
<223> OTHER INFORMATION: Primer

<400> SEQUENCE: 8
taatacgact cactataggg agcgtcctcc aggaatgaag aa          42

<210> SEQ ID NO 9
<211> LENGTH: 438
<212> TYPE: RNA
<213> ORGANISM: Diaphornia citri

<400> SEQUENCE: 9
ugagcugagg acgauugaug auuucagcca aaucuacugc aagggagaac uucuggacaa    60
gguacagcga ggaaacgugu uuccaaacga cucgaaaucg uuugucgauc ucaaacugaa   120
acagccagag gacgugauuc uggccaaguu ccgagccuug cucaccaaua augcugaucc   180
cgacaccacc acacugacca acuuugucaa cgaauacuuu gaagcaggca augagcugca   240
agucuggagu ccuccagauu ucaccuccaa cccgaguauc gagaacaaaa ucuccgacgc   300
caaauacaga caguuugccc ucgaccugaa ccaaauuugg aaagaguugg gccgcauagu   360
aaaacaagau guaagggaca acccucaacu guacucacuc auauacacac ccaauggauu   420
cuucauuccu ggaggacg                                                438

<210> SEQ ID NO 10
<211> LENGTH: 438
<212> TYPE: RNA
<213> ORGANISM: Diaphornia citri

<400> SEQUENCE: 10
acucgacucc ugcuaacuac uaaagucggu uuagaugacg uucccucuug aagaccuguu 60
ccaugucgcu ccuuugcaca aagguuugcu gagcuuuagc aaacagcuag aguuugacuu 120
ugucggucuc cugcacuaag accgguucaa ggcucggaac gagugguuau uacgacuagg 180
gcuguggugg ugugacuggu ugaaacaguu gcuuaugaaa cuucguccgu uacucgacgu 240
ucagaccuca ggaggucuaa aguggagguu gggcucauag cucuuguuuu agaggcugcg 300
guuuaugucu gucaaacggg agcuggacuu gguuuaaacc uuucucaacc cggcguauca 360
uuuuguucua cauucccugu ugggaguuga caugagugag uauaugugug gguuaccuaa 420
gaaguaagga ccuccugc 438

<210> SEQ ID NO 11
<211> LENGTH: 730
<212> TYPE: DNA
<213> ORGANISM: Diaphornia citri

<400> SEQUENCE: 11
tcaatgcgat ccttcagatg aacgctaact atctgagcga atggtggctc aaatttggca 60
acaaggattt gagtgccaag tacaagaaga ttgcgtacca actgcttgaa gccattcatg 120

```
aggttctatg gaatgaacag gttggtgtat ggctagacta cgacattaag aacaagaagc      180
cccgaaatta tttctacgtc tcaaacataa ctcctctgtg acattgagc tacaaattct       240 ccaaacaata tgtggctgag agagtactgc agtatttgcg agacaatgaa atcatcacca     300
aggacaatca agtgaaattc tatggtaccc ctacctcctt gttcaactct actcaacaat    360
gggattaccc taatgcctgg gccccactac aggcattcat catacaaggc ttggactaca    420
cgcaagacaa attagcaaag caagtggcat accgactggc tgaaaagtgg ctcttcacaa    480
actatatggg ctatgaaact agcaaggcta tgtttgagaa atatgatgta gaactcattg     540
gaaagacagg taatggaggt gagtacgagg cacaaactgg atttggttgg accaatggat    600
tcgcatttga gcttctaaat agatacggaa aaactatatc tttcaacaat actcaaggaa    660
gctactacaa taaaatcccc ggatccggtt acttatccgg ctattatccg tctttcatgt     720
ccggaagacc                                                           730

<210> SEQ ID NO 12
<211> LENGTH: 42
<212> TYPE: DNA
<213> ORGANISM: Artificial Sequence
<220> FEATURE:
<223> OTHER INFORMATION: Primer

<400> SEQUENCE: 12
taatacgact cactataggg agtcaatgcg atccttcaga tg                       42

<210> SEQ ID NO 13
<211> LENGTH: 42
<212> TYPE: DNA
<213> ORGANISM: Artificial Sequence
<220> FEATURE:
<223> OTHER INFORMATION: Primer

<400> SEQUENCE: 13
taatacgact cactataggg agggtcttcc ggacatgaaa ga                       42

<210> SEQ ID NO 14
<211> LENGTH: 730
<212> TYPE: RNA
<213> ORGANISM: Diaphornia citri

<400> SEQUENCE: 14
ucaaugcgau ccuucagaug aacgcuaacu aucugagcga auggugggcuc aaauuuggca     60 acaaggauuu gagugccaag uacaagaaga uugcguacca acugcuugaa gccauucaug    120
agguucuaug gaaugaacag guuggguguau ggcuagacua cgacauuaag aacaagaagc    180
cccgaaauua uuucuacguc ucaaacauaa cuccucugug acauugagc uacaaauucu     240 ccaaacaaua uguggcugag agaguacugc aguauuugcg agacaaugaa aucaucacca    300
aggacaauca agugaaauuc uaugguaccc cuaccuccuu guucaacucu acucaacaau    360
gggauuaccc uaaugccugg gccccacuac aggcauucau cauacaaggc uuggacuaca    420
cgcaagacaa auuagcaaag caaguggcau accgacuggc ugaaaagugg cucuucacaa    480
acuauauggg cuaugaaacu agcaaggcua uguuugagaa auaugaugua gaacucauug    540
gaaagacagg uaauggaggu gaguacgagg cacaaacugg auugguugg accaauggau    600 ucgcauuuga gcuucuaaau agauacggaa aaacuauauc uuucaacaau acucaaggaa    660
gcuacuacaa uaaaaucccc ggauccgguu acuuauccgg cuauuauccg ucuuucaugu    720
```
ccggaagacc                                                                    730

<210> SEQ ID NO 15
<211> LENGTH: 730
<212> TYPE: RNA
<213> ORGANISM: Diaphornia citri

<400> SEQUENCE: 15
aguuacgcua ggaagucuac uugcgauuga uagacucgcu uaccaccgag uuuaaaccgu      60
uguuccuaaa cucacgguuc auguucuucu aacgcauggu ugacgaacuu cgguaaguac     120
uccaagauac cuuacuuguc caaccacaua ccgaucugau gcuguaauuc uguucuucg      180 gggcuuuaau aaagaugcag aguuuguauu gaggagacac cuguaacucg auguuuaaga    240
gguuuguuau acaccgacuc ucucaugacg ucauaaacgc ucuguacuu uaguaguggu      300 uccuguuagu ucacuuuaag auaccauggg gauggaggaa caaguugaga ugaguuguua    360
cccuaauggg auuacggacc cggggugaug uccguaagua guauguuccg aaccugaugu    420 gcguucguu uaaucguuuc guucaccgua uggcugaccg acuuuccacc gagaaguguu      480
ugauauaccc gauacuuuga ucguuccgau acaaacucuu uauacuacau cuugaguaac    540
cuuucugucc auuaccucca cucaugcucc guguuugacc uaaaccaacc ugguuaccua    600
agcguaaacu cgaagauuua ucuaugccuu uuugauauag aaaguuguua ugaguuccuu    660
cgaugauguu auuuuagggg ccuaggccaa ugaauaggcc gauauaggc agaaaguaca     720 ggccuucugg                                                                    730

<210> SEQ ID NO 16
<211> LENGTH: 447
<212> TYPE: DNA
<213> ORGANISM: Diaphornia citri

<400> SEQUENCE: 16
atggtttctg gtgcaaagca acataatgga gcccctgcca aaaagaacct ccaggctctt     60
ccttttggaa atttgaaact ggttggttgg gatttggaca ccactgggcg tcgcttaatt    120
gatgaaattt gccagatatc tggttacaca ccagaggaaa gtttcaacat gtacataatg    180
ccacacagag acattgacct cagatccaag cgccgacatg ctctccgcac tgtgaatgct    240
ggcaagttcc gtgttttgaa agacaacaag actaacaaag tattgaggac aaaaagtgaa    300
atttcagctt taacagattt ccttgaatgg ctagagaagg tccgtggtga caatccaact    360
gtctacattg tgctcctctg ccatgagaca tacaagttga atgcttctct cctgcttgaa    420
gctttaagac gaaaccaaat gctggac                                                  447

<210> SEQ ID NO 17
<211> LENGTH: 41
<212> TYPE: DNA
<213> ORGANISM: Artificial Sequence
<220> FEATURE:
<223> OTHER INFORMATION: Primer

<400> SEQUENCE: 17
taatacgact cactataggg agatggtttc tggtgcaaag c                                  41

<210> SEQ ID NO 18
<211> LENGTH: 42
<212> TYPE: DNA
<213> ORGANISM: Artificial Sequence
<220> FEATURE:
<223> OTHER INFORMATION: Primer -continued

<400> SEQUENCE: 18
taatacgact cactataggg aggtccagca tttggtttcg tc 42

<210> SEQ ID NO 19
<211> LENGTH: 448
<212> TYPE: RNA
<213> ORGANISM: Diaphornia citri

<400> SEQUENCE: 19
aaugguuucu ggugcaaagc aacauaaugg agccccugcc aaaaagaacc uccaggcucu 60
uccuuuugga aauuugaaac ugguugguug ggauuuggac accacugggc gucgcuuaau 120
ugaugaaauu ugccagauau cugguuacac accagaggaa aguuucaaca uguacauaau 180
gccacacaga gacauugacc ucagauccaa gcgccgacau gcucuccgca cugugaaugc 240
uggcaaguuc cguguuuuga aagacaacaa gacuaacaaa guauugagga caaaaaguga 300
aauuucagcu uuaacagauu uccuugaaug gcuagagaag guccguggug acaauccaac 360
ugucuacauu gugcuccucu gccaugagac auacaaguug aaugcuucuc uccugcuuga 420
agcuuuaaga cgaaaccaaa ugcuggac 448

<210> SEQ ID NO 20
<211> LENGTH: 448
<212> TYPE: RNA
<213> ORGANISM: Diaphornia citri

<400> SEQUENCE: 20
uuaccaaaga ccacguuucg uuguauuacc ucggggacgg uuuuucuugg agguccgaga 60
aggaaaaccu uuaaacuuug accaaccaac ccuaaaccug uggugacccg cagcgaauua 120
acuacuuuaa acggucuaua gaccaaugug uggucuccuu ucaaaguugu acauguauua 180
cggugugucu cuguaacugg agucuagguu cgcggcugua cgagaggcgu gacacuuacg 240
accguucaag gcacaaaacu uucuguuguu cugauuguuu cauaacuccu guuuuucacu 300
uuaaagucga aauugucuaa aggaacuuac cgaucucuuc caggcaccac uguuagguug 360
acagauguaa cacgaggaga cgguacucug uauguucaac uuacgaagag aggacgaacu 420
ucgaaauucu gcuuugguuu acgaccug 448

<210> SEQ ID NO 21
<211> LENGTH: 266
<212> TYPE: DNA
<213> ORGANISM: Diaphornia citri

<400> SEQUENCE: 21
gttcactgga gctaggagtg gaattcagtc taagaagttc cttctccctg tttgcttttc 60
actgcttctc aatagcaatt ctgtttctgc tgcttcaaca agcaaatctc tcaagagaat 120
ggcatctgta aagctgtctg ctgatgaaag actgagtaaa cttgaaccca ttttgaaatc 180
aggatggaaa ttggttgaga acagggatgc tatttataaa gaataccttt tcaagaattt 240
caatgaggca tttggtttca tgacaa 266

<210> SEQ ID NO 22
<211> LENGTH: 43
<212> TYPE: DNA
<213> ORGANISM: Artificial Sequence
<220> FEATURE:
<223> OTHER INFORMATION: Primer

<400> SEQUENCE: 22
taatacgact cactataggg aggttcactg gagctaggag tgg    43

<210> SEQ ID NO 23
<211> LENGTH: 42
<212> TYPE: DNA
<213> ORGANISM: Artificial Sequence
<220> FEATURE:
<223> OTHER INFORMATION: Primer

<400> SEQUENCE: 23
taatacgact cactataggg agttgtcatg aaaccaaatg cc    42

<210> SEQ ID NO 24
<211> LENGTH: 266
<212> TYPE: RNA
<213> ORGANISM: Diaphornia citri

<400> SEQUENCE: 24
guucacugga gcuaggagug gaauucaguc uaagaaguuc cuucucccug uuugcuuuuc    60
acugcuucuc aauagcaauu cuguuucugc ugcuucaaca agcaaaucuc ucaagagaau    120
ggcaucugua aagcugucug cugaugaaag acugaguaaa cuugaaccca uuuugaaauc    180
aggauggaaa uugguugaga acagggaugc uauuuauaaa gaauaccuuu ucaagaauuu    240
caaugaggca uuugguuuca ugacaa    266

<210> SEQ ID NO 25
<211> LENGTH: 266
<212> TYPE: RNA
<213> ORGANISM: Diaphornia citri

<400> SEQUENCE: 25
caagugaccu cgauccucac cuuaagucag auucuucaag gaagagggac aaacgaaaag    60
ugacgaagag uuaucguuaa gacaaagacg acgaaguugu ucguuuagag aguucucuua    120
ccguagacau uucgacagac gacuacuuuc ugacucauuu gaacuuggguu aaaacuuuag    180 uccuaccuuu aaccaacucu ugucccuacg auaaauauuu cuuauggaaa aguucuuaaa    240
guuacuccgu aaaccaaagu acuguu    266

<210> SEQ ID NO 26
<211> LENGTH: 1908
<212> TYPE: DNA
<213> ORGANISM: Diaphornia citri

<400> SEQUENCE: 26
atggtgctat ctgagaccgt cactgaaact gtcacggaga cgttaccctc cggcactgac    60
gaggcagaca agatcagtct cattgctctg atgattttc taccctgccc agtggcggag    120
gatgcacagg gtgcgggcca ttatttgggc gaaaagtctt cgtcacctga gctgaggacg    180
attgatgatt tcagccaaat ctactgcaag ggagaacttc tggacaaggt acagcgagga    240
aacgtgtttc caaacgactc gaaatcgttt gtcgatctca aactgaaaca gccagaggac    300
gtgattctgg ccaagttccg agccttgctc accaataatg ctgatcccga caccaccaca    360
ctgaccaact tgtcaacga atactttgaa gcaggcaatg agctgcaagt ctggagtcct    420
ccagatttca cctccaaccc gagtatcgag aacaaaatct ccgacgccaa atacagacag    480
tttgccctcg acctgaacca aatttggaaa gagttgggcc gcatagtaaa acaagatgta    540
agggacaacc ctcaactgta ctcactcata tacacaccca atggattctt cattcctgga    600

-continued

```
ggacggtttc gagaactgta ctactgggat acgtactgga ttgtgcaagg tattctcctc    660
tgtgatatga aagactccgc caggggcgtg atcgagaaca taatcagtct cgtagatcag    720
ttcggtttca tgcctaacgg agctcgagtg tactatttgg aacgctctca gccgccactg    780
cttattccaa tggctgctag ctacgctaag tatacgggcg acaccaactt tataagaacc    840
caccttaagt cactaaccaa cgagtttgaa tactggatga agagacatat ggtcactgta    900
gagaaaaatg gcaagtacta caccatggct cgatactacg ctccgtccag aggccctagg    960
cccgagtctt acagagagga ctaccatgag gcagcagatt tgcagacaga ggatgagaaa   1020
aacttcctgt actcagagct gaaggcaggt gccgaaaccg gatgggactt ttccagtcgg   1080
tggttcatcg cacgggacgg tagcaataga ggaggcctca atacattcg caccacatcg    1140 atcattcccg tggacctcaa tgcgatcctt cagatgaacg ctaactatct gagcgaatgg   1200
tggctcaaat tggcaacaa ggatttgagt gccaagtaca agaagattgc gtaccaactg    1260
cttgaagcca ttcatgaggt tctatggaat aacaggttg gtgtatggct agactacgac    1320
attaagaaca agaagccccg aaattatttc tacgtctcaa acataactcc tctgtggaca   1380
ttgagctaca aattctccaa acaatatgtg gctgagagag tactgcagta tttgcgagac   1440
aatgaaatca tcaccaagga caatcaagtg aaattctatg gtaccsctac ctccttgttc   1500
aactctactc aacaatggga ttaccctaat gcctgggccc cactacaggc attcatcata   1560
caaggcttgg actacacgca agacaaatta gcaaagcaag tggcataccg actggctgaa   1620
aagtggctct tcacaaacta tgggctat gaaactagca aggctatgtt tgagaaatat     1680
gatgtagaac tcattggaaa gacaggtaat ggaggtgagt acgaggcaca aactggattt   1740
ggttggacca atggattcgc atttgagctt ctaaatagat acggaaaaac tatatctttc   1800
aacaatactc aaggaagcta ctacaataaa atccccggat ccggttactt atccggctat   1860
tatccgtctt tcatgtccgg aagaccttcc ttcatgtctg ctggataa              1908
```

<210> SEQ ID NO 27
<211> LENGTH: 1494
<212> TYPE: DNA
<213> ORGANISM: Diaphornia citri

<400> SEQUENCE: 27

```
gggaagggaa aagtcgaaag tcggcatttt tttttttactt tttgcttcaa gtgatcgaaa     60
agttgtaggt ttcttttcttc tttcgtaagt tctctttatt gaagtaagac tcatatttcc    120
acaaaaatgg tttctggtgc aaagcaacat aatggagccc ctgccaaaaa gaacctccag   180
gctcttcctt ttggaaattt gaaactggtt ggttgggatt tggacaccac tgggcgtcgc   240
ttaattgatg aaatttgcca gatatctggt tacacaccag aggaaagttt caacatgtac   300
ataatgccac acagagacat tgacctcaga tccaagcgcc gacatgctct ccgcactgtg   360
aatgctggca gttccgtgt tttgaaagac aacaagacta caaagtatt gaggacaaaa    420 agtgaaattt cagcttaac agatttcctt gaatggctag agaaggtccg tggtgacaat   480
ccaactgtct acattgtgct cctctgccat gagacataca agttgaatgc ttctctcctg   540
cttgaagctt taagacgaaa ccaaatgctg gacagattct ccaacattgt caaaggattt   600
gctgactgtc attctcttgc caaagacaag tgccagaagt caattgttgc atacgacctc   660
cgtaccctgt gcaagatgct tctgaacaag gagaatgcca gtctggcctc agcctctgag  720
cgtgccaagt atgcctacca gattgttgaa catctatgtg ctggtggtgt agagaatagc  780
```

```
gaaggcaacg ttggagcagg aggagactca gcagtgactc cctcacccga tgtcacaatc    840
aagactgttc tggcatatgc ttctgacatt gaagctgagg agaataacat acaggagttt    900
aaagtcaccc tggaacgtca gaacacactg aaacctgtgt tctactttgg actcaagacc    960
aaaaactaca aggaccgaca gcaagtcatg caactccgta gttacgtcac taacgcactt   1020
attgattacg aacagttgca gaatgtttgg acaaaccaga atggtaaaga aggcattgaa   1080
cagctcatca atacgaaatt gagtgaggtg gaagagaagg atcgtgaaac catcattgac   1140
tacattgtga agcactttga ggatcctaca gcctatgaga aagctagaca accacgcgtc   1200
aggcgtagca gacgtagccg ctcgggggaa tacgagaaaa agaagacaa caaggaaaat    1260 tccagcaacg aagacaaaga ggactccaaa caaaatggaa actaaatact tgatttaaaa   1320
tttattataa aaatattttt aaagttcact gttatggaag taagaaaaaa gaaagagaaa   1380
aaaaaaacac tcatacttat ttctgctttt aaagtataat gtcaaactca acagaaatct   1440
ttgtctcttc aaaatatgga tattgaaaaa aaaaaaaatc atttattcct ggaa         1494

<210> SEQ ID NO 28
<211> LENGTH: 429
<212> TYPE: DNA
<213> ORGANISM: Diaphornia citri

<400> SEQUENCE: 28
atgttcactg gagctaggag tggaattcag tctaagaagt tccttctccc tgtttgcttt     60
tcactgcttc tcaatagcaa ttctgttcct gctgcttcaa caagcaaatc tctcaagaga    120
atggcatctg taaagctgtc tgctgatgaa agactgagta aacttgaacc catttttgaaa   180 tcaggatgga aattggttga gaacagggat gctatttata agaataccct tttcaagaat    240
ttcaatgagg catttggttt catgacaaga actgcactct tggctgaaaa aatggatcat    300
catccagaat ggttcaatgt ttacaacaaa gttcaagtta ctctaagcac tcatgattgt    360
aatggtctca gcaataaaga tatcaaactt gcctcattca tggatacaat aatcaaagct    420
gaatcttaa                                                            429

<210> SEQ ID NO 29
<211> LENGTH: 635
<212> TYPE: PRT
<213> ORGANISM: Diaphornia citri

<400> SEQUENCE: 29

Met Val Leu Ser Glu Thr Val Thr Glu Thr Val Thr Glu Thr Leu Pro
1               5                   10                  15

Ser Gly Thr Asp Glu Ala Asp Lys Ile Ser Leu Ile Ala Leu Asp Asp
                20                  25                  30

Phe Leu Pro Cys Pro Val Ala Glu Asp Ala Gln Gly Ala Gly His Tyr
            35                  40                  45

Leu Gly Glu Lys Ser Ser Ser Pro Glu Leu Arg Thr Ile Asp Asp Phe
        50                  55                  60

Ser Gln Ile Tyr Cys Lys Gly Glu Leu Leu Asp Lys Val Gln Arg Gly
65                  70                  75                  80

Asn Val Phe Pro Asn Asp Ser Lys Ser Phe Val Asp Leu Lys Leu Lys
                85                  90                  95

Gln Pro Glu Asp Val Ile Leu Ala Lys Phe Arg Ala Leu Leu Thr Asn
            100                 105                 110

Asn Ala Asp Pro Asp Thr Thr Thr Leu Thr Asn Phe Val Asn Glu Tyr
        115                 120                 125
```

```
Phe Glu Ala Gly Asn Glu Leu Gln Val Trp Ser Pro Pro Asp Phe Thr
    130                 135                 140

Ser Asn Pro Ser Ile Glu Asn Lys Ile Ser Asp Ala Lys Tyr Arg Gln
145                 150                 155                 160

Phe Ala Leu Asp Leu Asn Gln Ile Trp Lys Glu Leu Gly Arg Ile Val
                165                 170                 175

Lys Gln Asp Val Arg Asp Asn Pro Gln Leu Tyr Ser Leu Ile Tyr Thr
            180                 185                 190

Pro Asn Gly Phe Phe Ile Pro Gly Gly Arg Phe Arg Glu Leu Tyr Tyr
        195                 200                 205

Trp Asp Thr Tyr Trp Ile Val Gln Gly Ile Leu Leu Cys Asp Met Lys
    210                 215                 220

Asp Ser Ala Arg Gly Val Ile Glu Asn Ile Ile Ser Leu Val Asp Gln
225                 230                 235                 240

Phe Gly Phe Met Pro Asn Gly Ala Arg Val Tyr Tyr Leu Glu Arg Ser
                245                 250                 255

Gln Pro Pro Leu Leu Ile Pro Met Ala Ala Ser Tyr Ala Lys Tyr Thr
            260                 265                 270

Gly Asp Thr Asn Phe Ile Arg Thr His Leu Lys Ser Leu Thr Asn Glu
        275                 280                 285

Phe Glu Tyr Trp Met Lys Arg His Met Val Thr Val Glu Lys Asn Gly
    290                 295                 300

Lys Tyr Tyr Thr Met Ala Arg Tyr Tyr Ala Pro Ser Arg Gly Pro Arg
305                 310                 315                 320

Pro Glu Ser Tyr Arg Glu Asp Tyr His Glu Ala Ala Asp Leu Gln Thr
                325                 330                 335

Glu Asp Glu Lys Asn Phe Leu Tyr Ser Glu Leu Lys Ala Gly Ala Glu
            340                 345                 350

Thr Gly Trp Asp Phe Ser Ser Arg Trp Phe Ile Ala Arg Asp Gly Ser
        355                 360                 365

Asn Arg Gly Gly Leu Lys Tyr Ile Arg Thr Thr Ser Ile Ile Pro Val
    370                 375                 380

Asp Leu Asn Ala Ile Leu Gln Met Asn Ala Asn Tyr Leu Ser Glu Trp
385                 390                 395                 400

Trp Leu Lys Phe Gly Asn Lys Asp Leu Ser Ala Lys Tyr Lys Lys Ile
                405                 410                 415

Ala Tyr Gln Leu Leu Glu Ala Ile His Glu Val Leu Trp Asn Glu Gln
            420                 425                 430

Val Gly Val Trp Leu Asp Tyr Asp Ile Lys Asn Lys Pro Arg Asn
        435                 440                 445

Tyr Phe Tyr Val Ser Asn Ile Thr Pro Leu Trp Thr Leu Ser Tyr Lys
    450                 455                 460

Phe Ser Lys Gln Tyr Val Ala Glu Arg Val Leu Gln Tyr Leu Arg Asp
465                 470                 475                 480

Asn Glu Ile Ile Thr Lys Asp Asn Gln Val Lys Phe Tyr Gly Thr Pro
                485                 490                 495

Thr Ser Leu Phe Asn Ser Thr Gln Gln Trp Asp Tyr Pro Asn Ala Trp
            500                 505                 510

Ala Pro Leu Gln Ala Phe Ile Ile Gln Gly Leu Asp Tyr Thr Gln Asp
        515                 520                 525

Lys Leu Ala Lys Gln Val Ala Tyr Arg Leu Ala Glu Lys Trp Leu Phe
    530                 535                 540
```

```
Thr Asn Tyr Met Gly Tyr Glu Thr Ser Lys Ala Met Phe Glu Lys Tyr
545                 550                 555                 560

Asp Val Glu Leu Ile Gly Lys Thr Gly Asn Gly Gly Glu Tyr Glu Ala
                565                 570                 575

Gln Thr Gly Phe Gly Trp Thr Asn Gly Phe Ala Phe Glu Leu Leu Asn
                580                 585                 590

Arg Tyr Gly Lys Thr Ile Ser Phe Asn Asn Thr Gln Gly Ser Tyr Tyr
            595                 600                 605

Asn Lys Ile Pro Gly Ser Gly Tyr Leu Ser Gly Tyr Tyr Pro Ser Phe
        610                 615                 620

Met Ser Gly Arg Pro Ser Phe Met Ser Ala Gly
625                 630                 635
```

DOUBLE STRANDED RNA COMPOSITIONS FOR REDUCING ASIAN CITRUS PSYLLID INFESTATION AND METHODS OF USE

CROSS REFERENCE TO RELATED APPLICATION

This application is related to and claims priority to U.S. Patent Application No. 62/287,315 filed on Jan. 26, 2016, the contents of which are incorporated herein.

BACKGROUND OF THE INVENTION

Sequence Listing

The Sequence Listing submitted via EFS-Web as ASCII compliant text file format (.txt) filed on Jan. 25, 2017, named "SequenceListing_ST25", (created on Jan. 22, 2016, 24 KB), is incorporated herein by reference. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

Field of the Invention

This invention relates to double stranded RNA and compositions containing double stranded RNA (dsRNA) to reduce the fitness and/or increase mortality of *Diaphorina citri*. (Asian citrus psyllid, Hemiptera: Liviidae) thereby reducing infestation of *D. citri* on citrus plants, and thereby reducing transmission of plant pathogens for which *D. citri* is a vector. One example of such microorganisms are *Candidatus Liberibacter* species. The invention also relates to methods of reducing the fitness and/or increasing mortality of *D. citri* by applying dsRNA as topical sprays, soil treatment, or other delivery methods to plants on which *D. citri* feeds. The invention also relates to genetically altered plants that express the dsRNA described herein; and to genetically altered microorganisms that express the dsRNA described herein.

Description of Related Art

Huanglongbing (HLB) (also called "citrus greening disease") is the most serious disease that threatens citrus crops worldwide. It is especially devastating to the U.S. and Florida citrus industries. The causative agents of HLB are *Candidatus Liberibacter* species of bacteria. This includes *Candidatus Liberibacter* africanus (CLaf), *Candidatus Liberibacter* asiaticus (CLas), and *Candidatus Liberibacter* americanus (CLam), however, until 2015 only CLas was found in U.S. The CLas and CLam bacteria are transmitted from plant to plant via Asian citrus psyllid (ACP; *D. citri*). The CLaf bacteria is transmitted from plant to plant via the psyllid Trioza enytreae. This disease is devastating the citrus industry in Florida because no effective treatments currently exists. Furthermore, both the causative pathogen and the insect vector have spread to other parts of the U.S. (California, Texas, Arizona) as well as to other citrus-producing countries/regions (Brazil, Asia, Middle East, China). Further, *Murraya paniculata* and other plants also host CLam and/or CLas. *D. citri* feed on these infected plants and carry the bacteria to non-infected plants. A list of these host plants could be found in freshfromflorida.com/content/download/24041/486974/hostlist.pdf. As such, the need exists for a composition and methods to stop the transmission of the disease. One approach to preventing disease transmission is to increase the mortality of ACP, the vector for the bacteria. Another approach is to reduce the fitness of ACP. Reducing ACP populations, by increasing mortality or reducing fitness, is the goal, thereby reducing transmission of the bacteria and the disease. One approach for reducing ACP populations, while not reducing beneficial insects, is to use RNAi technology.

Fire, et al. (U.S. Pat. No. 6,506,559) disclose a process of introducing RNA into a living cell to inhibit gene expression of a target gene in that cell. This cellular mechanism was named RNA interference, or RNAi. The RNA has a region with double-stranded structure. Inhibition is sequence-specific in that the nucleotide sequences of the duplex region of the RNA and of a portion of the target gene are identical. Specifically, Fire, et al. (U.S. Pat. No. 6,506,559) disclose a method to inhibit expression of a target gene in a cell, the method involves introducing a double-stranded ribonucleic acid, dsRNA, into the cell in an amount sufficient to trigger the RNAi process which leads to inhibition of specific protein translation of the target gene's messenger RNA (mRNA). One strand of the dsRNA trigger has a sequence which corresponds to the nucleotide sequence of the target mRNA. The dsRNA triggers the cell's natural defense mechanism, defined as RNA interference (RNAi), which uses the dsRNA trigger (designed dsRNA herein), to produce the guide strand small interfering RNA (siRNA) which is incorporated into the RNA-induced silencing complex (RISC) which is a multiprotein complex, specifically a ribonucleoprotein, which incorporates one strand of a double-stranded RNA (dsRNA) fragment. The RISC siRNA complex causes degradation of the targeted mRNA, thereby preventing translation into a protein. As used herein, a "trigger" is any dsRNA molecule that causes RNAi activity against a specific gene.

One mechanism of action involves a long trigger (i.e., a long dsRNA) being cleaved by an enzyme called "dicer" to produce several siRNA that are shorter in length than the dsRNA. The size of these smaller siRNA is believed to range from about 19 base pairs to about 25 base pairs, but the most common classes of siRNA contain 21 base pairs or 24 base pairs (Hamilton, et al., 2002 *EMBO J.*, 21:4671-4679). However, others have determined that the siRNA can be shorter than 19 base pairs. See, e.g., Guleda, et al., *Geno. Proteomic Bioinfo.*, 184(6)183-199 (2011). The siRNA molecules are each then incorporated into RISC. The duplex RNA is unwound leaving the anti-sense strand to guide RISC to complementary mRNA for subsequent endonucleolytic cleavage. This results in the reduction of the corresponding protein that would have been made from the targeted and degraded mRNA. Thus, this is commonly referred to as gene-silencing or downregulation.

A few RNAi sequences have been identified and are currently being evaluated for (i) reducing ACP vector capacity to host CLas, and (ii) nymph and/or adult survival. See, e.g., El-Shesheny, et al. (2013) PLoS ONE 8(5): e65392 (doi.org/10.1.3711journal.pone.0065392); and Killiny, et al. (2014) PLoS ONE 9(10): e110536 (doi.org/10.1371/journal.pone.0110536). Li, et al., *Insect Sci.*, 20:31-39 (2013) reviews attempts to use RNAi to control Hemiptera and the overall lack of success of killing Hemiptera via this technique.

One goal of using RNAi is that if one selects a RNA sequence that is relatively unique to the target pest (in this case, *D. citri*) and which is effective in reducing expression of the target gene such that increased mortality of the target pest occurs, then the treatments can avoid harming beneficial insects, such as pollinators, predators, and parasitoid species. This invention successfully meets these goals in that the dsRNA sequence for ACP trehalase mRNA target (described herein) appears to be unique to ACP and does not harm bees or other pollinators. Trehalase hydrolyzes the disaccharide α,α-trehalose to two molecules of D-glucose. α,α-trehalose is the main sugar found in insect hemolymph (insect blood), and it has a critical role in energy production and biosynthesis of macromolecules including chitin. Trehalase has been purified and characterized from several different insects where it is found in soluble (Tre-1) and membrane-bound (Tre-2) forms encoded by distinct genes. The soluble form is found in hemolymph and the bound form is found in many different insect tissues See, Lee, et al., (2007) *Biosci Biotechnol Biochem* 71(9);2256-65.

The coding sequence of ACP trehalase (hereinafter "trehalase") was obtained by automated computational analysis from a *D. citri* genomic sequence (NW_007377674.1), annotated using the gene prediction method Gnomon (NCBI, Rockville, Md.). See also, Reese, et al. (2013) *J. Genomics* 2:54-58; doi: 10,7150/jgen.7692. Supporting evidence includes similarity to 16 proteins, and 100% coverage of the annotated genomic feature by RNAseq alignments, including 5 samples with support for all annotated introns. Comparative analysis of the coding sequence of trehalase with other insects genomic sequences indicate that it corresponds to Tre-1 (soluble form of trehalase), as it shares higher homology to other known insects soluble trehalase homologs (*Aphis glycines*, GenBank: mRNA: JQ246351.1/ protein: AFJ00065.1, *Nilaparvata lugens*, mRNA: H790319.1/protein: ACN85420.1; *Locusta migratoria*, mRNA: H795020.1/protein: ACP28173,1). See, Reese, et al. (2013) *J. Genomics* 2:54-58 (doi: 10.715/gen.7692); Hunter, et al. (2009) *Open Entomol.* 3:18-29; Hunter, et al. (2008) Florida Entomology Society meeting, abstracts, p.11 (flaentsoc.org/2008annmeetabstracts.pdf); and Hunter, et al. (2014) *J. Citrus Pathology* 1:4.7 (Proc. 3$^{rd}$ Int'l Res. Conf, Huanglongbing, Orlando, Fla.). The cDNA sequence of trehalase is in SEQ ID NO: 26.

A need exists for reducing transmission of CLas and/or CLam to non-infected plants, and in particular, citrus plants. A method of reducing fitness and survival of *D. citri* (and thereby reducing *D. citri* infestation) reduces the number of infected *D. citri* that can transmit HLB pathogens to uninfected plants, thereby slowing down or stopping pathogen transmission and disease spread. Furthermore, any solution to this problem which does not reduce beneficial insects, such as predators and parasitoids of psyllids, as well as beneficial pollinators, will have the added benefits of biological control pressures that will help suppress psyllid populations.

BRIEF SUMMARY OF THE INVENTION

It is an object of this invention to have a dsRNA that reduces the fitness and/or increases the mortality (or reduces the survival) of *D. citri* after the *D. citri* ingests the dsRNA. This dsRNA contains a sense region containing between approximately sixteen nucleotides and 1908 nucleotides, and an anti-sense region complementary to the sense region. The anti-sense region is also complementary to *D. citri* trehalase cDNA or a fragment of *D. citri* trehalase cDNA. This *D. citri* trehalase cDNA has the sequence of SEQ ID NO: 26 or encodes *D. citri* trehalase having the amino acid sequence of SEQ ID NO: 29. The fragment of *D. citri* trehalase cDNA has the sequence of SEQ ID NO: 1, SEQ ID NO: 6, or SEQ ID NO. 11. It is another object of this invention that the sense region of this dsRNA has a sequence of between 16 nt and 469 nt of SEQ ID NO: 4, between 16 nt and 438 nt of SEQ ID NO: 9, between 16 nt and 730 nt of SEQ ID NO: 14, or between 16 nt and 1908 nt of the RNA equivalent of SEQ ID NO: 26.

It is another object of this invention to have a *D. citri* trehalase dsRNA solution that contains an agriculturally acceptable carrier and *D. citri* trehalase dsRNA. It is another object of this invention that one strand of the *D. citri* trehalase dsRNA has one of the following sequences: between 16 nt and 469 nt of SEQ ID NO: 4, between 16 nt and 438 nt of SEQ ID NO: 9, between 16 nt and 730 nt of SEQ ID NO: 14, between 16 nt and 1908 nt of the RNA equivalent of SEQ ID NO: 26, and between 16 nt and 1908 nt of the RNA equivalent of a cDNA encoding *D. citri* trehalase having an amino acid sequence of SEQ ID NO: 29. It is a further object of this invention that the agriculturally acceptable carrier of the dsRNA solution can be water, surfactant, liposome, lipid, protein, peptide, nanotube, chitin, inactivated microorganism, or a combination thereof. This dsRNA solution can also contain a compound that prevents dsRNA degradation, a translaminar chemical, a mineral, a clay, a fertilizer, a sugar, or a combination thereof.

It is an object of this invention to have a method of reducing *D. citri* infestation on a treated plant (the number of *D. citri* that feed of the treated plant) compared to the *D. citri* infestation on an untreated plant (the number of *D. citri* that feed of the untreated plant) by administering the *D. citri* trehalase dsRNA solution described supra to an untreated plant in an amount effective to kill *D. citri* that ingest or absorb the dsRNA solution to generate a treated plant, and allowing the *D. citri* to ingest or absorb the dsRNA solution and thereby killing the *D. citri* that ingested or absorbed the dsRNA solution. This dsRNA solution contains an agriculturally acceptable carrier and *D. citri* trehalase dsRNA which has insecticidal activity against *D. citri*, thereby reducing the *D. citri* infestation on the treated plant compared the *D. citri* infestation on the untreated plant. In one embodiment of this invention, the administering step involves spraying the *D. citri* trehalase dsRNA solution onto the untreated plant to generate the treated plant. In another embodiment of this invention, the administering step involves applying the *D. citri* trehalase dsRNA solution to the soil surrounding the untreated plant to allow for the roots of the untreated plant to absorb the *D. citri* trehalase dsRNA solution and/or the *D. citri* dsRNA, thereby generating the treated plant. An alternative embodiment of this invention, the administering step involves applying the *D. citri* trehalase dsRNA solution to one or more roots of the untreated plant and the roots absorbs the *D. citri* trehalase dsRNA solution and/or the *D. citri* dsRNA to generate the treated plant.

It is an object of this invention to have a method for reducing the fitness or survival of *D. citri* that feed on an altered plant that contains a *D. citri* trehalase dsRNA by introducing the *D. citri* trehalase dsRNA into a wild-type plant upon which the *D. citri* feeds, thereby producing the altered plant containing the *D. citri* trehalase dsRNA, and allowing *D. citri* to feed on the altered plant containing the *D. citri* trehalase dsRNA and ingest the *D. citri* trehalase dsRNA, such that the *D. citri* trehalase dsRNA reduces the fitness or survival of *D. citri* that ingest the *D. citri* trehalase dsRNA. In one embodiment of this invention, the *D. citri* trehalase dsRNA has one of the following sequences: between 16 nt and 469 nt of SEQ II) NO: 4, between 16 nt and 438 nt of SEQ ID NO: 9, between 16 nt and 730 nt of SEQ ID NO: 14, between 16 nt and 1908 nt of the RNA equivalent of SEQ ID NO: 26, and between 16 nt and 1908 nt of the RNA equivalent of a cDNA encoding *D. citri* trehalase having amino acid sequence of SEQ ID NO: 29.

The introducing of the *D. citri* trehalase dsRNA into the wild-type plant can occur by spraying a dsRNA solution containing the *D. citri* trehalase dsRNA onto the wild-type plant; by applying the dsRNA solution containing the *D. citri* trehalase dsRNA to the roots of the wild-type plant, or by applying the dsRNA solution containing the *D. citri* trehalase dsRNA to the soil around the wild-type plant so that the roots of the wild-type plant absorb the *D. citri* trehalase dsRNA solution and/or the *D. citri* trehalase dsRNA. This dsRNA solution can also contain an agriculturally acceptable carrier (such as water, surfactant, liposome, lipid, protein, peptide, nanotube, chitin, inactivated microorganism, or a combination thereof) or other compounds (such as, a compound that prevent dsRNA degradation, a translaminar chemical, a mineral, a clay, a fertilizer, a sugar, or a combination thereof).

It is another object of this invention to have a method for reducing the fitness or survival of *D. citri* that feed on an altered plant that contains a *D. citri* trehalase dsRNA by introducing an expression vector encoding *D. citri* trehalase dsRNA into a wild-type plant cell upon which the *D. citri* feeds, thereby producing an altered plant cell, selecting an altered plant cell that produces the *D. citri* trehalase dsRNA, inducing the altered plant cell that produces the *D. citri* trehalase dsRNA to grow into an altered plant that produces and contains the *D. citri* trehalase dsRNA, and allowing *D. citri* to feed on the altered plant containing the *D. citri* trehalase dsRNA and ingest the *D. citri* trehalase dsRNA, such that the *D. citri* trehalase dsRNA reduces the fitness or survival of *D. citri* that ingest the *D. citri* trehalase dsRNA. In this embodiment, the expression vector has at least one heterologous promoter operably linked a polynucleotide that contains a sense region and an anti-sense region. It is a further object of this invention that the sequence of the sense region is between 16 nt and 469 nt of SEQ ID NO: 1, between 16 nt and 438 nt of SEQ ID NO: 6, between 16 nt and 730 nt of SEQ ID NO: 11, between 16 nt and 1908 nt of the RNA equivalent of SEQ ID NO: 26, and between 16 nt and 1908 nt of the RNA equivalent of a cDNA encoding *D. citri* trehalase having amino acid sequence of SEQ ID NO: 29. Furthermore, the anti-sense region has a sequence complementary to the sequence of the sense region. In one embodiment of the invention, one promoter controls transcription of the sense region and the anti-sense region. In another embodiment, one promoter controls transcription of the sense region, and a second promoter controls transcription of the anti-sense region.

It is another object of this invention to have a method of reducing transmission by *D. citri* of a disease-causing microorganism from a treated plant to an untreated plant by applying the dsRNA solution described supra to a wild-type plant to produce the treated plant, and allowing *D. citri* to feed on the treated plant and ingest or absorb the dsRNA solution, such that the dsRNA solution contains an agriculturally acceptable carrier and a *D. citri* trehalase dsRNA, and such that the *D. citri* trehalase dsRNA kills the *D. citri* that ingests or absorbs the *D. citri* trehalase dsRNA, because dead *D. citri* are unable to transmit the disease-causing microorganism to an untreated plant. It is a further object of this invention that the *D. citri* trehalase dsRNA has one of the sequences described above. The step of applying the dsRNA solution to the wild-type plant occurs by (i) spraying the dsRNA solution onto the wild-type plant, (ii) applying the dsRNA solution to the roots of the wild-type plant, and/or (iii) applying the dsRNA solution to the soil around the wild-type plant so that the roots of the wild-type plant absorb the dsRNA solution containing the *D. citri* trehalase dsRNA.

It is an object of this invention to have a genetically altered plant, and parts thereof (i.e., leaves, flowers, stems, roots, cell, pollen, protoplast, etc.), that contain an expression vector which has a first promoter operably linked to a *D. citri* trehalase sense polynucleotide and a second promoter operably linked to a *D. citri* trehalase anti-sense polynucleotide, such that the *D. citri* trehalase sense polynucleotide and the *D. citri* trehalase anti-sense polynucleotide are complementary to each other. The *D. citri* trehalase sense polynucleotide has a sequence of between 16 nt and 469 nt of SEQ ID NO: 1, between 16 nt and 438 nt of SEQ ID NO: 6, between 16 nt and 730 nt of SEQ ID NO: 11, between 16 nt and 1908 nt of SEQ ID NO: 26, and/or between 16 nt and 1908 nt of a cDNA encoding *D. citri* trehalase having the amino acid sequence of SEQ ID NO: 29. In one embodiment, the first promoter and the second promoter are the same promoters. In another embodiment, the first promoter and the second promoter are different promoters.

It is another object of this invention to have a genetically altered plant, and parts thereof (i.e., leaves, flowers, stems, roots, cell, pollen, protoplast, etc.), that contains an expression vector having a promoter operably linked to a polynucleotide which has a *D. citri* trehalase sense region and a *D. citri* trehalase anti-sense region, such that the *D. citri* trehalase anti-sense region is complementary to the *D. citri* trehalase sense region. The *D. citri* trehalase sense polynucleotide has a sequence of between 16 nt and 469 nt of SEQ ID NO: 1, between 16 nt and 438 nt of SEQ ID NO: 6, between 16 nt and 730 nt of SEQ ID NO: 11, between 16 nt and 1908 nt of SEQ ID NO: 26, and/or between 16 nt and 1908 nt of a cDNA encoding *D. citri* trehalase having the amino acid sequence of SEQ ID NO: 29.

It is an object of this invention to have a method for making a genetically altered plant that produces a *D. citri* trehalase dsRNA by transforming a wild-type plant cell with a *D. citri* trehalase dsRNA producing expression vector to generate a genetically altered plant cell that produces the *D. citri* trehalase dsRNA, and growing the genetically altered plant cell that produces the *D. citri* trehalase dsRNA to produce the genetically altered plant that produces the *D. citri* trehalase dsRNA. Two *D. citri* trehalase dsRNA producing expression vectors are described supra. It is another object of this invention to have a genetically altered plant, and parts thereof (i.e., leaves, flowers, stems, roots, cell, pollen, protoplast, etc.), produced by this method and that produce *D. citri* trehalase dsRNA. It is a further object of this invention to have a genetically altered plant cell of this genetically altered plant.

It is another object of this invention to have a cDNA encoding *D. citri* trehalase with the sequence of SEQ ID NO: 26. It is another object of this invention to have an expression vector containing a heterologous promoter operably linked to a polynucleotide that encodes *D. citri* trehalase having the amino acid sequence of SEQ ID NO: 29.

It is another object of this invention to utilize the method of virus-induced gene silencing for plant gene to reduce transmission by *D. citri* of one or more disease-causing microorganisms from a treated plant to an untreated plant by the killing of *D. citri* or by reducing the fitness or survival of *D. citri*. It is a further object of this invention to have a recombinant virus containing a heterologous polynucleotide that encodes *D. citri* trehalase, a fragment thereof, and/or a sequence that is the reverse complementary thereof, such that the recombinant virus can be used to infect a plant in need of treatment and produce dsRNA based on the sequence of the heterologous polynucleotide during infection of the plant. The virus can be a DNA virus or an RNA virus. The heterologous polynucleotide can have a sense region; a sense region and an anti-sense region which is complementary to the sense region; or a sense region, an anti-sense region, and a linker. It is another object of this invention to generate an altered plant that can produce the dsRNA described hereby by infecting a wild-type plant with the recombinant virus that can produce the dsRNA described herein. In one embodiment, the recombinant virus is a recombinant *Citrus tristeza* virus.

BRIEF DESCRIPTION OF THE FIGURES

FIG. 1 is the DNA sequence of nucleotides 809 to 1277 (SEQ :ID NO: 1) of trehalase cDNA (SEQ ID NO: 26) which encodes the sense strand of dsRNA trehalase #1. The bolded and underlined nucleotides are contained in the forward and reverse primers, respectively (SEQ ID NOs: 2 and 3).

FIG. 2 is the DNA sequence of nucleotides 168 to 605 (SEQ ID NO: 6) of trehalase cDNA (SEQ ID NO: 26) which encodes the sense strand of dsRNA trehalase #2. The bolded and underlined nucleotides are contained in the forward and reverse primers, respectively (SEQ ID NOs: 7 and 8).

FIG. 3 is the DNA sequence of nucleotides 1157 to 1886 (SEQ ID NO: 11) of trehalase cDNA (SEQ ID NO: 26) which encodes the sense strand of dsRNA trehalase #3. The bolded and underlined nucleotides are contained in the forward and reverse primers, respectively (SEQ II) NOs: 12 and 13).

DETAILED DESCRIPTION OF THE INVENTION

The *D. citri* trehalase gene sequence is not identical to trehalase sequences in various beneficial insects which could be analyzed. As such, the use of *D. citri* trehalase dsRNA (or fragments of trehalase dsRNA) to reduce fitness and survival of *D. citri* provides a mechanism for reducing the spread of *C. Liberibacter* species and other microorganisms for which *D. citri* are a host from infected plants to uninfected plants without harming beneficial insects. Non-limiting example of such other microorganisms for which *D. citri* are carriers include reovirus. See, Marutani-Hert, et al. (2009) *Florida Entomologist* 92:314-320. Accordingly, the dsRNA can be administered to plants, or produced by genetically altered plants, or by microbes (bacteria/yeast/viruses/fungi etc.). The inventions described herein include the dsRNA described herein, compositions containing the dsRNA described herein, genetically altered plants or microbes that produce the dsRNA described herein, methods for generating the genetically altered plants, and methods of using the dsRNA described herein to reduce fitness and survival of *D. citri* populations and thereby reduce *D. citri* infestation, and also thereby reduce the transmission of microorganisms that infect plants, such as but not limited to *C. Liberibacter* species, by psyllid species, and more specifically by *D. citri*.

Table 1 provides an explanatory list of the sequences discussed herein and include for *D. citri* trehalase cds and dsRNA sequences; maternal protein exuperantia cds and dsRNA sequences; and pterin-4-alpha-carbinolamine dehydratase (PCBD1) cds and dsRNA sequences; and the primers used. Note that three cds for trehalase, each covering different sections of trehalase cds are listed in Table 1 and used in the examples, below.

TABLE 1

| | |
|---|---|
| SEQ ID NO: 1 | Coding DNA sequence of sense strand of trehalase dsRNA #1 corresponding to nucleotides 809-1277 of trehalase |
| SEQ ID NO: 2 | 5' sense primer for SEQ ID NO: 1 where nucleotides 1-22 are T7 promoter sequences and nucleotides 23-42 are trehalase sequences |
| SEQ ID NO: 3 | 3' anti-sense primer for SEQ ID NO: 1 where nucleotides 1-22 are T7 promoter sequences and nucleotides 23-42 are trehalase sequences |
| SEQ ID NO: 4 | RNA sequence of sense strand for trehalase dsRNA #1 |
| SEQ ID NO: 5 | RNA sequence of anti-sense strand of trehalase dsRNA #1 |
| SEQ ID NO: 6 | Coding DNA sequence of sense strand of trehalase dsRNA #2 corresponding to nucleotides 168-605 of trehalase |
| SEQ ID NO: 7 | 5' sense primer for SEQ ID NO: 6 where nucleotides 1-22 are T7 promoter sequences and nucleotides 23-42 are trehalase sequences |
| SEQ ID NO: 8 | 3' anti-sense primer for SEQ ID NO: 6 where nucleotides 1-22 are T7 promoter sequences and nucleotides 23-42 are trehalase sequences |
| SEQ ID NO: 9 | RNA sequence of sense strand for trehalase dsRNA #2 |
| SEQ ID NO: 10 | RNA sequence of anti-sense strand for trehalase dsRNA #2 |
| SEQ ID NO: 11 | Coding DNA sequence of sense strand of trehalase dsRNA #3 corresponding to nucleotides 1157-1886 of trehalase |
| SEQ ID NO: 12 | 5' sense primer for SEQ ID NO: 11 where nucleotides 1-22 are T7 promoter sequences and nucleotides 23-42 are trehalase sequence |
| SEQ ID NO: 13 | 3' anti-sense primer for SEQ ID NO: 11 where nucleotides 1-22 are T7 promoter sequences and nucleotides 23-42 are trehalase sequences |
| SEQ ID NO: 14 | RNA sequence of sense strand for trehalase dsRNA #3 |
| SEQ ID NO: 15 | RNA sequence of anti-sense strand for trehalase dsRNA #3 |
| SEQ ID NO: 16 | Coding DNA sequence of sense strand of maternal protein exuperantia dsRNA corresponding to nucleotides 1-447 of material protein exuperantia |
| SEQ ID NO: 17 | 5' sense primer for SEQ ID NO: 16 where nucleotides 1-22 are T7 promoter sequences and nucleotides 23-41 are maternal protein exuperantia sequence |
| SEQ ID NO: 18 | 3' anti-sense primer for SEQ ID NO: 16 where nucleotides 1-22 are T7 promoter sequences and nucleotides 23-42 are material protein exuperantia sequences |
| SEQ ID NO: 19 | RNA sense strand for maternal protein exuperantia dsRNA |
| SEQ ID NO: 20 | RNA antisense strand for maternal protein exuperantia dsRNA |
| SEQ ID NO: 21 | Coding DNA sequence of sense strand of pterin-4-alpha-carbinolamine dehydratase (PCBD1) dsRNA corresponding to nucleotides 3-268 of PCBD1 |

TABLE 1-continued

| | |
|---|---|
| SEQ ID NO: 22 | 5' sense primer for SEQ ID NO: 21 where nucleotides 1-22 are T7 promoter sequences and nucleotides 23-43 are PCBD1 sequence |
| SEQ ID NO: 23 | 3' anti-sense primer for SEQ ID NO: 21 where nucleotides 1-22 are T7 promoter sequences and nucleotides 23-42 are PCBD1 sequences |
| SEQ ID NO: 24 | RNA sense strand for PCBD1 dsRNA |
| SEQ ID NO: 25 | RNA antisense strand for PCBD1 dsRNA |
| SEQ ID NO: 26 | trehalase cDNA sequence |
| SEQ ID NO: 27 | exuperantia cDNA sequence |
| SEQ ID NO: 28 | PCBD1 cDNA sequence |
| SEQ ID NO: 29 | trehalase amino acid sequence |

Because this invention involves production of genetically altered plants and involves recombinant DNA techniques, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "gene" refers to a DNA sequence involved in producing a RNA or polypeptide or precursor thereof. The polypeptide or RNA can be encoded by a full-length coding sequence (cds) or by intron-interrupted portions of the coding sequence, such as exon sequences. In one embodiment of the invention, the gene target is the trehalase mRNA in ACP. The polynucleotide cds sequence of trehalase is SEQ ID NO: 26.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, peptide-nucleic acids (PNAs) and bridged nucleic acid (RNA, 2'-O'-aminoethylene bridged nucleic acid. See, e.g., Rahman, et al. (2007) *Nucleosides Nucleotides Nucleic Acids* 26:1625-1628). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp), or nucleotides (nt). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Unless otherwise indicated, a particular nucleic acid sequence also implicitly encompasses conservatively modified variants thereof (e.g., degenerate codon substitutions), the complementary (or complement) sequence, and the reverse complement sequence, as well as the sequence explicitly indicated. Specifically, degenerate codon substitutions may be achieved by generating sequences in which the third position of one or more selected (or all) codons is substituted with mixed-base and/or deoxyinosine residues (see e.g., Batzer et al., *Nucleic Acid Res.* 19:5081 (1991); Ohtsuka et al., *J. Biol. Chem.* 260:2605-2608 (1985); and Rossolini et al., *Mol. Cell. Probes* 8:91-98(1994)). Because of the degeneracy of nucleic acid codons, one can use various different polynucleotides to encode identical polypeptides. Table 2. infra, contains information about which nucleic acid codons encode which amino acids.

TABLE 2

| Amino acid | Nucleic acid codons |
|---|---|
| Ala/A | GCT, GCC, GCA, GCG |
| Arg/R | CGT, CGC, CGA, CGG, AGA, AGG |
| Asn/N | AAT, AAC |
| Asp/D | GAT, GAC |
| Cys/C | TGT, TGC |
| Gln/Q | CAA, CAG |
| Glu/E | GAA, GAG |
| Gly/G | GGT, GGC, GGA, GGG |
| His/H | CAT, CAC |
| Ile/I | ATT, ATC, ATA |
| Leu/L | TTA, TTG, CTT, CTC, CTA, CTG |
| Lys/K | AAA, AAG |
| Met/M | ATG |
| Phe/F | TTT, TTC |
| Pro/P | CCT, CCC, CCA, CCG |
| Ser/S | TCT, TCC, TCA, TCG, AGT, AGC |
| Thr/T | ACT, ACC, ACA, ACG |
| Trp/W | TGG |
| Tyr/Y | TAT, TAC |
| Val/V | GTT, GTC, GTA, GTG |

The term "primer" refers to an oligonucleotide, which is capable of acting as a point of initiation of synthesis when placed under conditions in which primer extension is initiated. A primer may occur naturally, as in a purified restriction digest, or may be produced synthetically.

A primer is selected to be "substantially complementary" to a strand of specific sequence of the template. A primer must be sufficiently complementary to hybridize with a template strand for primer elongation to occur. A primer sequence need not reflect the exact sequence of the template.

For example, a non-complementary nucleotide fragment may be attached to the 5' end of the primer, with the remainder of the primer sequence being substantially complementary to the strand. Non-complementary bases or longer sequences can be interspersed into the primer, provided that the primer sequence is sufficiently complementary with the sequence of the template to hybridize and thereby form a template primer complex for synthesis of the extension product of the primer.

"dsRNA" refers to double-stranded RNA that comprises a sense region and an antisense region of a selected target gene (or sequences with high sequence identity thereto so that gene silencing can occur), as well as any smaller double-stranded RNAs formed therefrom by RNAse or Dicer activity. Such dsRNA can include portions of single-stranded RNA, but contains at least 18 base pairs of dsRNA. A dsRNA after been processed by Dicer generates siRNAs (18-25 by in length) that are double-strand, and could contain ends with 2 nucleotide overhangs, which will be single-stranded. It is predicted that usually siRNA around 21 nt in length (or, alternatively, between 17 and 27 nt in length), will be incorporated into RISC. In one embodiment, the sense region and the antisense region of a dsRNA are on the same strand of RNA and are separated by a linker. In this embodiment, when the sense region and the anti sense region anneal together, the dsRNA contains a loop which is the linker. One promoter operably linked to the DNA or RNA encoding both the sense region and the antisense region is used to produce the one RNA molecule containing both the sense region and the anti-sense region. In another embodiment, the sense region and the antisense region are present on two distinct strands of RNA (a sense strand and the anti-sense strand which is complementary to the sense strand) which anneal together to form the dsRNA. In this embodiment, a promoter is operably linked to each strand of DNA or RNA; where one DNA or RNA strand encodes the RNA containing the sense region and the other strand of DNA or RNA encodes the RNA containing the anti-sense region. In this embodiment, the promoter on each strand can be the same as or different from the promoter on the other strand. After the RNAs are transcribed, two RNA strands anneal together because the sense region and the anti-sense region are complementary to each other, thus forming the dsRNA. In yet another embodiment, one strand of DNA or RNA can encode both the sense region and the anti-sense region of the dsRNA. However, the DNA or RNA coding each region are separated from each other so that two promoters are necessary to transcribe each region. That is, the DNA or RNA encoding the anti-sense region and the DNA or RNA encoding the sense region are operably linked to their own promoter. Again, the two promoters can be the same promoter or different promoters. In one embodiment, the promoter can be a T7 RNA polymerase promoter. Other promoters are well-known in the art and can be used (see discussion infra). While many embodiments of this invention use DNA to encode the sense region and/or anti-sense region, as described infra, it is possible to use a recombinant RNA virus to produce the dsRNA described herein. In such case, the genome virus is RNA which has been altered to have one of the sequences of *D. citri* trehalse described herein or reverse complement thereof.

Regarding the specificity, it is driven by the siRNA. There are two publications that addressed this issue in insects. One publication shows that to be specific, a siRNA should share a minimum of at least 19 nt in length with the target mRNA. See, Whyard, et al. (2009) *Insect Biochem Molecul. Biol.* 39:824-32. The second publication shows that it is necessary to share a contiguous sequence length of 20 nt or longer, between the dsRNA and the target mRNA for efficacy in degradation (silencing). See, Bachman, et al. (2013) *Transgenic Res.* 22:1207-22.

Active dsRNA molecules have worked when they were as long as 1,000 bp, and should work when even longer. For the purposes of the inventions described herein, any siRNA having at least 19 nt :length derived from SEQ ID NO: 1, SEQ ID NO: 6, SEQ ID NO: 11, SEQ ID NO: 16 and SEQ ID NO: 21 will be specific to ACP. This region is specific to ACP, because across the active trigger there are no regions of 25 nt or longer which is 100% identical to any known insect, animal, human or plant species sequence. In one embodiment the dsRNA can be any 16, 17, 18, 19, 20, 21, 22, 23, 24, 25, 26, 27, 28, 29, 30, 31, 32, 33, 34, 35, 36, 37, 38, 39, 40, 45, 50, 55, 60, or longer contiguous nucleotides of *D. citri* trehalase cDNA (SEQ ID NO: 26) or of SEQ ID NOs: 1, 6, and 11, up to and including all 469 nt of SEQ ID NO: 1, up to and including all 438 nt of SEQ ID NO: 6, up to and including all 730 nt of SEQ ID NO: 11, and up to and including all 1908 nt of SEQ ID NO: 26. In alternative embodiments, the dsRNA can range in length between 16 bp and 30 bp, between 16 bp and 25 bp, between 18 and 30 bp, and between 19 bp and 28 bp. In yet another embodiment, RNA forms that are created by RNAse III family (Dicer or Dicer-like ribonuclease) or Dicer activity that are longer dsRNA are within the scope of this invention.

siRNA can be synthetically made, expressed and secreted directly from a transformed cell, or microbe, or can be generated from a longer dsRNA by enzymatic activity. These siRNAs can be blunt-ended or can have 1 bp to 4 bp overlapping ends of various nucleotide combinations. Also modified microRNAs comprising a portion of the putative trehalase gene and its complementary sequence are included herein as dsRNAs. For clarification, "bp" is an abbreviation for "basepairs" and "nt" is an abbreviation for "nucleotide".

In one embodiment of this invention, dsRNA is used to control ACP without such dsRNA being co-delivered with a transfection-promoting agent, although in some embodiments the dsRNA of the invention can be provided in a solution with a transfection-promoting agent. In one embodiment of the invention, the dsRNA is expressed in a plant to be protected, or expressed in microorganisms which can be endemic organisms of the plant (microbes, virus, phytoplasma, viroids, fungal, protists) or free-living microbes (yeasts, bacteria, protists, fungi) any of which are delivered, alive, dead or processed, via root treatments, or foliar sprayed on plants, or injected into plants, which are to be protected. Alternatively, the microorganism can be a transgenic organism endemic to the plant and deliver dsRNA to the plant. See, e.g., Subhas, et al. (2014) *J. Biotech.* 176:42-49 for an example of virus induced gene silencing using *Citrus tristeza* virus. See, also, Tenllado, et at (2003) *BMC Biotechnol* 3:3 for an example of a crude extract of a bacterial cell culture containing dsRNA that protects plants against viral infections.

In one embodiment, a dsRNA solution is administered to the plant on which *D. citri* feed. A dsRNA solution contains one or more of the dsRNAs discussed herein and an agriculturally acceptable carrier. An agriculturally acceptable carrier can be water, one or more liposomes, one or more lipids, one or more surfactants, one or more proteins, one or more peptides, one or more nanotubes, chitin, and/or one or more inactivated microorganisms that encapsulate the dsRNA. See WO 2003/004644 for examples of other agriculturally acceptable carriers. The dsRNA solution can also contain one or more sugars, compounds that assist in preventing dsRNA degradation, translaminar chemicals, chemical brighteners, clays, minerals, and/or fertilizers. One can spray the dsRNA solution on plants (leaves, branches, trunk, exposed roots, etc.) which the D. citri will ingest or absorb when on the plant. One can apply the dsRNA solution to the soil around the plant so that the plant's roots absorb the dsRNA solution and transport it to other parts of the plants. Then when *D. citri* feed on the plant, they will ingest the dsRNA (and perhaps other components of the dsRNA solution) in the dsRNA solution when feeding on the plant. Alternatively, one or more roots can be placed in a container which contains the dsRNA solution so that those roots absorb the dsRNA solution. The dsRNA solution can also be injected into the plant. As such, the dsRNA solution can be in a spray dsRNA solution, a drenching dsRNA solution, or an injectable dsRNA solution. Other types of solutions are known in the art.

The term "chimeric" and "fusion" when referring to a gene or polynucleotide are used to refer to a gene or polynucleotide containing at least two functionally relevant DNA/RNA polynucleotides (such as promoter, 5'UTR, coding region, 3'UTR, and/or intron) that are not naturally associated with each other, such as a fusion of functionally relevant polynucleotides from different sources to form a plant-expressible chimeric polynucleotide that generates a dsRNA targeting AC P's trehalase transcript.

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

The terms "identical" or percent "identity", in the context of two or more polynucleotides or polypeptide sequences, refer to two or more sequences or sub-sequences that are the same or have a specified percentage of nucleotides or amino acids (respectively) that are the same (e.g., 80%, 85% identity, 90% identity, 99%, or 100% identity), when compared and aligned for maximum correspondence over a designated region as measured using a sequence comparison algorithm or by manual alignment and visual inspection.

The phrase "high percent identical " or "high percent identity", in the context of two polynucleotides or polypeptides, refers to two or more sequences or sub-sequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid identity, when compared and aligned for maximum correspondence, as measured using a sequence comparison algorithm or by visual inspection. In an exemplary embodiment, a high percent identity exists over a region of the sequences that is at least about 16 nucleotides or amino acids in length. In another exemplary embodiment, a high percent identity exists over a region of the sequences that is at least about 50 nucleotides or amino acids in length. In still another exemplary embodiment, a high percent identity exists over a region of the sequences that is at least about 100 nucleotides or amino acids or more in length. In one exemplary embodiment, the sequences are high percent identical over the entire length of the polynucleotide or polypeptide sequences.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algodthm then calculates the percent sequence identities for the test sequences relative to the reference sequence, based on the program parameters. Methods of aligninent of sequences for comparison are well-known in the art. Optimal alignment of sequences for comparison can be conducted, e.g., by the local homology algorithm of Smith & Waterman, *Adv. Appl. Math,* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of various algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al. (eds), *Current Protocols in Molecular Biology,* 1995 supplement).

The "complement" of a particular polynucleotide sequence is that nucleotide sequence which would be capable of forming a double-stranded DNA or RNA molecule with the represented nucleotide sequence, and which can be derived from the represented nucleotide sequence by replacing the nucleotides by their complementary nucleotide according to Chargaff's rules (A<>T; G<>C) and reading in the 5' to 3' direction, i.e., in opposite direction of the represented nucleotide sequence.

In one embodiment of the invention, sense and antisense RNAs and dsRNA can be separately expressed in-vitro or in-vivo. In-vivo production of sense and anti sense RNAs can use different chimeric polynucleotide constructs using the same or different promoters or using an expression vector containing two convergent promoters in opposite orientation. These sense and anti sense RNAs which are formed, e.g., in the same host cells, or synthesized, and can then combine to form dsRNA. It is clear that whenever reference is made herein to a dsRNA chimeric or fusion polynucleotide or a dsRNA molecule, that such dsRNA formed, e.g., in plant cells, from sense and antisense RNA produced separately is also included. Also synthetically made dsRNA annealing RNA strands are included herein when the sense and antisense strands are present together.

As used herein, the term "promoter" refers to a polynucleotide that in its native state is located upstream or 5' to a translational start codon of an open reading frame (or protein-coding region) and that is involved in recognition and binding of RNA polymerase and other proteins (trans-acting transcription factors) to initiate transcription. A "plant promoter" is a native or non-native promoter that is functional in plant cells, even if the promoter is present in a microorganism that infects plants or a microorganism that does not infect plants. The promoters that are predominately functional in a specific tissue or set of tissues are considered "tissue-specific promoters". A plant promoter can be used as a 5' regulatory element for modulating expression of a particular desired polynucleotide (heterologous polynucleotide) operably linked thereto. When operably linked to a transcribeable polynucleotide, a promoter typically causes the transcribeable polynucleotide to be transcribed in a manner that is similar to that of which the promoter is normally associated.

Plant promoters can include promoters produced through the manipulation of known promoters to produce artificial, chimeric, or hybrid promoters. Such promoters can also combine cis-elements from one or more promoters, for example, by adding a heterologous regulatory element to an active promoter with its own partial or complete regulatory elements. The term "cis-element" refers to a cis-acting transcriptional regulatory element that confers an aspect of the overall control of gene expression. A cis-element may function to bind transcription factors, trans-acting protein factors that regulate transcription. Some cis-elements bind more than one transcription factor, and transcription factors may interact with different affinities with more than one cis-element.

The term "vector" refers to DNA, RNA, a protein, or polypeptide that are to be introduced into a host cell or organism. The polynucleotides, protein, and polypeptide which are to be introduced into a host can be therapeutic or prophylactic in nature; can encode or be an antigen; can be regulatory in nature; etc. There are various types of vectors including viruses, viroids, plasmids, bacteriophages, cosmids, and bacteria.

An expression vector is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an "expression cassette". In contrast, as described in the examples herein, a "cassette" is a polynucleotide containing a section of an expression vector. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A heterologous polynucleotide sequence is operably linked to one or more transcription regulatory elements (e.g., promoter, terminator and, optionally, enhancer) such that the transcription regulatory elements control and regulate the transcription and/or translation of that heterologous polynucleotide sequence. A cassette can have the heterologous polynucleotide operably linked to one or more transcription regulatory elements. As used herein, the term "operably linked" refers to a first polynucleotide, such as a promoter, connected with a second transcribeable polynucleotide, such as a gene of interest, where the polynucleotides are arranged such that the first polynucleotide affects the transcription of the second polynucleotide. In some embodiments, the two polynucleotide molecules are part of a single contiguous polynucleotide. In other embodiments, the two polynucleotides are adjacent. For example, a promoter is operably linked to a gene of interest if the promoter regulates or mediates transcription of the gene of interest in a cell. Similarly a terminator is operably linked to the polynucleotide of interest if the terminator regulates or mediates transcription of the polynucleotide of interest, and in particular, the termination of transcription. Constructs of the present invention would typically contain a promoter operably linked to a transcribeable polynucleotide operably linked to a terminator.

The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes/polynucleotides that are not found within the native (non-recombinant or wild-type) form of the cell or express native genes in an otherwise abnormal amount over-expressed, under-expressed or not expressed at all compared to the non-recombinant or wild-type cell or organism. In particular, one can alter the genomic DNA of a wild-type plant by molecular biology techniques that are well-known to one of ordinary skill in the art and generate a recombinant plant.

The terms "transgenic", "transformed", "transformation", and "transfection" are similar in meaning to "recombinant". "Transformation", "transgenic", and "transfection" refer to the transfer of a polynucleotide into a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host's chromosome remain as an expression vector within the cell. One may need to grow the cell under certain growth or environmental conditions in order for the expression vector to remain in the cell or the cell's progeny. Further, for expression to occur the organism or cell may need to be kept under certain conditions. Genetically altered organisms or cells containing the recombinant polynucleotide can be referred to as "transgenic" or "transformed" organisms or cells or simply as "transformants", as well as recombinant organisms or cells.

A genetically altered organism is any organism with any changes to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has mutations in its DNA caused by the one or more mutagens, as compared to the wild-type organism (Le, organism not subjected to the mutagens). Also, an organism that has been bred to incorporate a mutation into its genetic material is a genetically altered organism.

Transformation and generation of genetically altered monocotyledonous and dicotyledonous plant cells is well known in the art. See, e.g., Weising, et al., *Ann. Rev. Genet.* 22:421-477 (1988); U.S. Pat. No. 5,679,558; *Agrobacterium Protocols*, ed: Gartland, Humana Press Inc. (1995); and Wang, et al. *Acta Hort.* 461:401-408 (1998). The choice of method varies with the type of plant to be transformed, the particular application and/or the desired result. The appropriate transformation technique is readily chosen by the skilled practitioner.

The polynucleotide encoding the putative trehalase (SEQ ID NO: 1) or a portion thereof, operably linked to one or two appropriate promoters, can be stably inserted in a conventional manner into the genome (cytoplasmic genome or nucleic genome) of a single plant cell, and the genetically altered plant cell can be used in a conventional manner to produce a genetically altered plant that produces the dsRNA of this invention which can reduce fitness and survival of ACP. In this regard, a disarmed Ti-plasmid, containing the polynucleotide of this invention, in *Agrobacterium tumefaciens* can be used to genetically alter the plant cell, and thereafter, a genetically altered plant can be regenerated from the genetically altered plant cell using the procedures described in the art, for example, in EP 0 116 718, EP 0 270 822, WO 84/02913 and EP 0 242 246. Plant regeneration from cultured protoplasts is described in Evans et al., *Protoplasts Isolation and Culture*, in *Handbook of Plant Cell Culture*, pp. 124-176, MacMillan Publishing Company, New York, 1983; and Binding, *Regeneration of Plants*, in *Plant Protoplasts*, pp. 21-73, CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467-486 (1987).

Preferred Ti-plasmid vectors each contain the polynucleotide encoding trehalase or a portion of trehalase between the border sequences, or at least located to the left of the right border sequence, of the T-DNA of the Ti-plasmid. Of course, other types of vectors can be used to transform the plant cell, using procedures such as direct gene transfer (as described, for example in EP 0 233 247), pollen mediated transformation (as described, for example in EP 0 270 356, WO 85/01856, and U.S. Pat. No. 4.684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140,553; Fromm, et al., *Bio/Technology* 8:833-839 (1990); Gordon-Kamm, et al., *The Plant Cell* 2:603-618 (1990) and rice (Shimamoto, et al., *Nature* 338:274-276 (1989); Datta et al., *Bio/Technology* 8:736-740 (1990)) and the method for transforming monocots generally (WO 92/09696). For cotton transformation, the method described in WO 00/71733 can be used. For soybean transformation, reference is made to methods known in the art, e.g., Hinchee, et al. (*Bio/Technology* 6:915 (1988)) and Christou, et al. (*Trends Biotechnology* 8:145 (1990)) or the method of WO 00/42207.

The resulting genetically altered plant can be used in a conventional plant breeding scheme to produce more genetically altered plants with the same characteristics or to introduce the polynucleotide encoding dsRNA trehalase in other varieties of the same or related plant species. Seeds, which are obtained from the genetically altered plants, contain the dsRNA trehalase gene as a stable genomic insert. Plants containing a dsRNA in accordance with the invention include plants having or derived from root stocks of plants containing the dsRNA trehalase gene of the invention, e.g., fruit trees or ornamental plants. Hence, any wild-type grafted plant parts inserted on a genetically altered plant or plant part are included in the invention because the RNAi activity is transported to these grafted parts, and any insects feeding on such grafted plant are similarly affected by the dsRNA or siRNA of the invention.

For a genetically altered plant that produces dsRNA, one constructs an expression vector or cassette (made from DNA) that encodes, at a minimum, a first promoter and the dsRNA sequence of interest such that the promoter sequence is 5' (upstream) to and operably linked to the dsRNA sequence. The expression vector or cassette may optionally contain a second promoter (same as or different from the first promoter) upstream and operably linked to the reverse complementary sequence of the dsRNA sequence such that two strands of RNA that are complementary to each other can be produced. Alternatively, the expression vector or cassette can contain one promoter operably linked to both the dsRNA sequence (sense strand) in question and the complement or reverse complement of the dsRNA sequence (anti-sense strand) in question, such that the transcribed RNA can bend on itself and the two desires sequences can anneal. Alternatively, a second expression vector or cassette (made from DNA) can encode, at a minimum, a second promoter (same as or different from the promoter) operably linked to the reverse complementary sequence of the dsRNA such that two strands of complementary RNA can be produced in the plant. The expression vector(s) or cassette(s) is/are inserted in a plant cell genome (nuclear or cytoplasmic). The promoter(s) used should be a promoter(s) that is/are active in a plant. Of course, the expression vector or cassette can have other transcription regulatory elements, such as enhancers, terminators, etc.

Promoters that are active in plants are well-known in the field. Such promoters can be constitutive, inducible, and/or tissue-specific. Non-limiting examples of constitutive plant promoters include 35S promoters of the cauliflower mosaic virus (CaMV) (e.g., of isolates CM 1841 (Gardner, et al., *Nucleic Acids Research* 9:2871-2887 (1981)), CabbB-S (Franck, et al., *Cell* 21:285-294 (1980)) and CabbB-JI (Hull and Howell, *Virology* 86:482-493 (1987))), ubiquitin promoter (e.g., the maize ubiquitin promoter of Christensen, et al., *Plant Mol. Biol.* 18:675-689 (1992)), gos2 promoter (de Pater, et al., *The Plant J.* 2:834-844 (1992)), emu promoter (Last, et al., *Theor. Appl. Genet.* 81:581-588 (1990)), actin promoter (see, e.g., An, et al., *The Plant J.* 110:107 (1996)) and Zhang, et al., *The Plant Cell* 3:1155-1165 (1991)); Cassava vein mosaic virus promoters (see, e.g., WO 97/48819 and Verdaguer, et al., *Plant Mol. Biol.* 37:1055-1067 (1998)), the pPLEX series of promoters from Subterranean Clover Stunt Virus (WO 96/06932, particularly the S4 or S7 promoter), alcohol dehydrogenase promoter (e.g., pAdh1S (GenBank accession numbers X04049, X00581)), and the TR1' promoter and the TR2' promoter which drive the expression of the 1' and 2' genes, respectively, of the T-DNA (Velten, et al., *EMBO J.* 3:2723-2730 (1984)). Tissue-specific promoters are promoters that direct a higher level of transcriptional expression in some cells or tissues of the plant than in other cells or tissue. Non-limiting examples of tissue-specific promoters include the phosphoenolpyruvate carboxylase (PEP or PPC1) promoter (Pathirana, et al., *Plant J.* 12:293-304 (1997), and Kausch, et al., *Plant Mol. Biol.* 45(1):1-15 (2001)), chlorophyll A/B binding protein (CAB) promoter (Bansal, et al., *Prot. Natl. Acad. Sci. USA* 89(8):3654-8 (1992)), small subunit of ribulose-1,5-bisphosphate carboxylase (ssRBCS) promoter (Bonsai, et al., *Proc. Natl. Acad. Sci. USA* 89(8):3654-8 (1992)), senescence activated promoter (SEE1) (Robson, et al., *Plant Biotechnol. J.* 2(2):101-12 (2004)), and sorghum leaf primoridia specific promoter (RS2) (GenBank Accession No. EI979305.1). These promoters (PPC1, CAB, ssRBCS, SSE1, and RS2) are all active in the aerial part of a plant. Further, the PPC1 promoter is a strong promoter for expression in vascular tissue and is one potential useful embodiment of the current invention. Furthermore, phloem specific promoters derived from citrus can be used to generate transgenic plants to drive the expression of dsRNA into the phloem. Some examples are the sucrose synthase-1 promoter (CsSUS1p and CsSUS1p-2) (Singer et al., *Planta* 234:623-637 (2011)) and the phloem protein-2 promoter (CsPP2) (Miyata et al., *Plant Cell Report* 31(11):2005-2013 (2012)) from *Citrus sinensis*. Alternatively, a plant-expressible promoter can also be a wound-inducible promoter, such as the promoter of the pea cell wall invertase gene (Zhang, et al., *Plant Physiol.* 112: 1111-1117 (1996)).

Other types of RNA polymerase promoters that can be used are promoters from microorganisms, such as, but not limited to the bacteriophage T7 RNA polymerase promoter, yeast Galactose (GLA1) promoter, yeast glyceraldehyde-3-phosphate dehydrogenase (GAP) promoter, yeast Alcohol Oxidase (AOX) promoter.

Other elements which can be used to increase transcription expression in plant cells include, but are not limited to, an intron (e.g., hsp70 intron) at the 5' end or 3' end of the chimeric gene, or in the coding sequence of the chimeric dsRNA gene (such as, between the region encoding the sense and antisense portion of the dsRNA), promoter enhancer elements, duplicated or triplicated promoter regions, 5' leader sequences different from the chimeric gene or different from an endogenous (plant host) gene leader sequence, 3' untranslated sequences different from the chimeric gene or different from an endogenous (plant host) 3' untranslated sequence.

The expression vector or cassette could contain suitable 3' untranslated transcription regulation sequences (i.e., transcript formation and polyadenylation sequences). Potential polyadenylation and transcript formation sequences include those sequences in the nopaline synthase gene (Depicker, et al., *J. Molec. Appl. Genetics* 1:561-573 (1982)), the octopine synthase gene (Gielen, et al., *EMBO J.* 3:835-845 (1984)), the SCSNI or the Malic enzyme terminators (Schunmann, et al., *Plant Functional Biology* 30:453-460 (2003)), and the T-DNA gene 7 (Velten and Schell, *Nucleic Acids Research* 13:6981-6998 (1985)).

In another embodiment of this invention, one can infect plants with either an RNA virus or DNA virus which can produce virus-related the siRNAs described herein in the plant's cells during replication of the virus which kills *D. citri* that feed on the infected plant. The dsRNA, either derived from a replication intermediate or secondary-structure characters of some single-stranded viral RNA region, can accumulate to high levels in virus-infected plant cells. In the case of plant DNA viruses, the dsRNA may be formed by annealing of overlapping complementary transcripts. See, Baulcombe (2004) Nature 431:356-363. This method, referred to as virus-induced gene silencing for plant gene (VIGS), offers an attractive alternative to genetically altered plants that produce dsRNA because VIGS allows the investigation of gene function without requiring plant transformation. See, e.g., Ruiz, et al. (1998) *Plant Cell* 10:937-946; and Burch-Smith, et al. (2004) *Plant Physiol.* 142:21-27. Recombinant plant viruses can be constructed to carry an inserted partial or whole sequence of a candidate gene (a heterologous polynucleotide) operably linked to a viral promoter. Such recombinant plant viruses can infect and move systemically in plants, producing dsRNA (which are then processed into siRNA by the plant's cells) or produce anti-sense RNA. The dsRNA and/or siRNA and/or anti-sense RNA can be ingested by an insect pest during its feeding, mediating suppression of the insect's endogenous gene transcripts. A VIGS derived from the *Citrus tristeza* virus (ON) expressing a fragment of the Abnormal wing disc (Awg) gene from *D. citri* was shown to induce RNAi effects on *D. citri* (Hajeri, et al. (2014) *J. of Biotech.* 176:42-49, doi:10.1016/j.jbiotec.2014.02.010). Insects that developed on *Citrus macrophylla* plants infected with the CTV-Awd had lower levels of corresponding mRNA, resulting malformed-wing phenotype in adults and increased adult mortality. In a similar approach, a recombinant CTV containing SEQ ID NO: 4 or SEQ ID NO: 5; SEQ ID NO: 9 or SEQ ID NO: 10; SEQ ID NO: 14 or SEQ ID NO: 15; the RNA equivalent of SEQ ID NO: 26 (as the candidate gene); the reverse complement thereof; and/or fragments thereof can be generated using reverse genetics or other techniques that are well-known in the art field. The recombinant CTV are then allowed to infect citrus plants and replicate, thereby producing RNA containing the anti-sense sequence and sense sequence of the candidate gene which form dsRNA. When *D. citri* feed on the infected plant, the psyllid will ingest the dsRNA, causing psyllid death.

In another embodiment, a recombinant virus contains the sense region and anti-sense region of trehalase gene (or fragments thereof) on one polynucleotide (can be an RNA virus or DNA virus). Then, during viral replication, the sense region and the anti-sense region anneal to each other, forming dsRNA. Again, when *D. citri* feed on the infected plant, the psyllid ingests the dsRNA causing psyllid death. In this embodiment the sense region and anti-sense region can optionally be separated by a linking region that separates the sense region and anti-sense such that a hair-pin loop can be formed upon annealing. In this embodiment, when the recombinant virus is an RNA virus (such as CTV), it contains RNA having the sequence of SEQ ID NO: 4 and SEQ ID NO: 5; SEQ ID NO: 9 and SEQ ID NO: 10; SEQ ID NO: 14 and SEQ ID NO: 15; the RNA equivalent of SEQ ID NO: 26 and its reverse complement; and/or fragments thereof. In this embodiment, when the recombinant virus is a DNA virus, it contains the DNA sequence of SEQ ID NO: 1, SEQ ID NO: 6, SEQ ID NO: 11, SEQ ID NO: 26, and/or fragments thereof, and the complementary sequence thereof. See, also, U.S. Patent Pub. 2013/0125254 Dawson et al.; and U.S. Patent Pub. 2015/0067918 Kress for more information regarding CTV VIGS. See, also, EP 2,730,657 A1 for additional information about VIGS.

"Insecticidal activity" of a dsRNA, as used herein, refers to the capacity to reduce fitness and/or survival of insects when the insects ingest or feed on the dsRNA, such reduction in fitness and/or survival is greater than the level of fitness and/or survival of insects that are not exposed to the dsRNA. "Insect-control" of a dsRNA, as used herein, refers to the capacity to inhibit the insect development, fertility, inhibition of pheromone production, or growth in such a manner that the insect population causes less damage to a plant, produces fewer offspring, are less fit, more susceptible to insect pathogens, or are more susceptible to predator attack, or are deterred from feeding on such plant, compared to the insect population that is untreated or to an insect population that feed on an untreated plant.

The term "plant" includes whole plants, plant organs, progeny of whole plants or plant organs, embryos, somatic embryos, embryo-like structures, protocorms, protocorm-like bodies (PLBs), and suspensions of plant cells. Plant organs comprise, e,g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The class of plants that can be used in the method of the invention is generally as broad as the class of higher and lower plants amenable to the molecular biology and plant breeding techniques described herein, specifically gymnosperms and angiosperms (monocotyledonous (monocots) and dicotyledonous (dicots) plants). It includes plants of a variety of ploidy levels, including aneuploid, polyploid, diploid, haploid and hemizygous. The plants described herein are citrus plants, such as but not limited to, orange, lemon, lime, tangerine, Persian lime, and grapefruit. Plants also include citrons and near relatives of citrus or citron plants. Other plants on which *D. citri* teed are included in this invention. Non-limiting examples of such other plants include *Aegle marmelos, Aeglopsis chevaliers, Afraegle gabonensis, Afraegle paniculata, Atalantia missionis, Atalantia monophylla, Balsamocitrus dawei, Citropsis gslletsaila, Citropsis schweinfurthii, Clausena anisum-olens, Clausena excavate, Clausena indica, Clausena lansium, Eremocitrus glauca, Fortunella crassifolia, Fortunella margarita, Fortunella polyandra, Limonia acidissima, Merrillia caloxylon, Microcitrus australasica, Microcitronella, Murraya exotica, Murraya koenigii, Murraya paniculata, Naringi crenulata, Pamburus missionis, Poncirus trifoliate, Severinia buxlfolia, Swinglea ghninosa, Toddalia asiatica, Triphasia trifolia, Vepris lanceolata, Zanthoxylum fagara.*

An "effective amount" is an amount sufficient to effect desired beneficial or deleterious results. An effective amount can be administered in one or more administrations. In terms of treatment, an "effective amount" is that amount sufficient to make the target pest non-functional by causing an adverse effect on that pest, including, but not limited to, physiological damage to the pest; inhibition or modulation of pest growth; inhibition or modulation of pest reproduction; or death of the pest. In one embodiment of the invention, the target insect ingests the dsRNA containing solution which disrupts production of critical protein(s) that are necessary for developmental, feeding, and/or reproductive functions of the insect.

The term "a nucleic acid consisting essentially of", "a dsRNA consisting essentially of", "a polynucleotide consisting essentially of", and grammatical variations thereof mean nucleic acids that differ from a reference nucleic acid sequence by 20 or fewer nucleotides and also perform the function of the reference nucleic acid sequence. Such variants include sequences which are shorter or longer than the reference nucleic acid sequence, have different residues at particular positions, or a combination thereof.

The terms "approximately" and "about" refer to a quantity, level, value or amount that varies by as much as 30% in one embodiment, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Many techniques involving molecular biology discussed herein are well-known to one of ordinary skill in the art and are described in, e.g., Green and Sambrook, *Molecular Cloning, A Laboratory Manual* 4th ed. 2012, Cold Spring Harbor Laboratory; Ausubel et al. (eds.), *Current Protocols in Molecular Biology*. 1994—current, John Wiley & Sons; and Kriegler, *Gene Transfer and Expression: A Laboratory Manual* (1993). Unless otherwise noted, technical terms are used according to conventional usage. Definitions of common terms in molecular biology maybe found in e.g., Benjamin Lewin, *Genes IX*, Oxford University Press, 2007 (ISBN 0763740632); Krebs, et al. (eds), *The Encyclopedia of Molecular Biology*, Blackwell Science Ltd., 1994 (ISBN 0-632-02182-9); and Robert A. Meyers (ed.), *Molecular Biology and Biotechnology: a Comprehensive Desk Reference*, VCH Publishers, Inc., 1995 (ISBN 1-56081-569-8).

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

EXAMPLE 1

Selection of Sequence and Production of dsRNA

*D. citri* trehalase sequence was obtained by automated computational analysis from a *D. citri* genomic sequence (GenBank NW_007377674.1), annotated using gene prediction method: Gnomon. Supporting evidence includes similarity to: 16 Proteins, and 100% coverage of the annotated genomic feature by RNAseq alignments, including 5 samples with support for all annotated introns. All sequences annotated as trehalase in the transcriptomic library were selected, aligned in order to check for possible sequencing errors, and finally the correct sequence was identified. The final sequence was submitted to another round of comparative analysis, which included: (1) sequencing and comparative analysis of nucleotide sequence using BLAST® analyses tools (NCBI website, blast.ncbi.nlm.nih.gov/Blast.cgi) to confirm that the sequence is from trehalase; (2) in silico translation to find the putative trehalase protein amino acid sequence; (3) followed by comparative analysis of the amino acid sequence with sequences contained on GenBank, Pfam, and Prosite websites, using various protein analyses tools to confirm the identity of the sequence. This analysis also shows that the amino acid sequence contains functional domains associated with other trehalase proteins.

With reference to *D. citri* trehalase gene, SEQ ID NO: 4, SEQ ID NO: 9 and SEQ ID NO: 14 are the sense strand sequence of double-stranded RNA polynucleotides designed with one strand that is capable of hybridizing to the mRNA transcribed from the *D. citri* trehalase gene at positions 168-605 (SEQ ID NO: 6), 809-1277 (SEQ ID NO: 1), and 1157-1886 (SEQ ID NO: 11). The three designed long dsRNAs were made using an Ambion MEGAscript RNAi. Kit (ThermoFisher Scientific, Waltham, Mass.).

With reference to *D. citri* maternal protein exuperantia gene, SEQ ID NO: 19 is the sense strand sequence of double-stranded RNA polynucleotides designed with one strand that is capable of hybridizing to the mRNA transcribed from the *D. citri* exuperantia transcript at positions 1-447 (SEQ ID NO: 16). The designed long dsRNAs were made using an Ambion MEGAscript RNAi Kit (ThermoFisher Scientific, Waltham, Mass.).

With reference to *D. citri* pterin-4-alpha-carbinolamine dehydratase transcript (PCBD1), SEQ ID NO: 24 is the sense strand sequence of double-stranded RNA polynucleotides designed with one strand that is capable of hybridizing to the snRNA transcribed from the *D. citri* ptetin-4-alpha-carbinolamine dehydratase transcript at positions 3-268 (SEQ ID NO: 21). The designed long dsRNAs were made using an Ambion MEGAscript RNAi Kit (ThermoFisher Scientific, Waltham, Mass.).

A cDNA encoding trehalase (SEQ ID NO: 26) was synthesized from *D. citri* total RNA extracted using Trizol (Invitrogen, Waltham, Mass.). Initially, cDNA was reversed transcribed from 5 μg of total RNA using SuperScript® III First-Strand Synthesis System (Invitrogen, Waltham, Mass.), using the random hexamers provided by the manufacturer. The region encoding nucleotides 809-1277 of trehalase (SEQ ID NO: 1) was amplified by PCR by combining the cDNA, the 5' primer (SEQ ID NO: 2) and the 3' primer (SEQ ID NO: 3) with DNA polymerase, nucleotides and the appropriated buffer per AmpliTaq Gold® 360 Master Mix Cat. No. 4398881 (Applied Biosystems, Waltham, Mass.) to generate an amplicon containing nucleotides 809-1277 of trehalase flanked by T7 RNA polymerase recognition sequence. FIG. 1 shows the sequence of SEQ ID NO: 1; the *D. citri* sequences contained in the 5' primer (SEQ ID NO: 2) and 3' primer (SEQ ID NO: 3) are bolded and underlined. The T7 RNA polymerase sequences in these primers are not present in FIG. 1. This amplicon was cloned into a pCR™2.1-TOPO® plasmid using the TOPO® TA cloning Kit, Cat. No. K4500J10 (Invitrogen, Waltham, Mass.). The plasmid (hereafter named pACP-Tr_1) was then transfected into One Shot TOP 10 competent *E. coli*. Using the above produced trehalase cDNA, the region encoding nucleotides 168-605 of trehalase (SEQ ID NO: 6) was amplified by PCR by combining the 5' primer (SEQ ID NO: 7) and the 3' primer (SEQ ID NO: 8) with DNA polymerase, nucleotides and the appropriated buffer per AmpliTaq Gold® 360 Master Mix Cat. No. 4398881 (Applied Biosystems, Waltham, Mass.) to generate an amplicon containing nucleotides 168-605 of trehalase flanked by T7 RNA polymerase recognition sequence. FIG. 2 shows the sequence of SEQ ID NO: 6; the *D. citri* sequences contained in the 5' primer (SEQ ID NO: 7) and 3' primer (SEQ ID NO: 8) are bolded and underlined. The T7 RNA polymerase sequences in these primers are not present in FIG. 2. This amplicon was then cloned into a pCR™2.1-TOPO® plasmid using the TOPO® TA cloning Kit, Cat. No. K4500J10 (Invitrogen, Waltham, Mass.). The plasmid (hereafter named pACP-Tr_2) was then transfected into One Shot TOP 10 competent *E. coli*. Also using the cDNA of trehalase produced above, the region encoding nucleotides 1157-1886 of trehalase (SEQ ID NO: 11) was amplified by PCR by combining the 5' primer (SEQ ID NO: 12) and the 3' primer (SEQ ID NO: 13) with DNA polymerase, nucleotides and the appropriated buffer per AmpliTaq Gold® 360 Master Mix Cat. No. 4398881 (Applied Biosystems, Waltham, Mass.) to generate an amplicon containing nucleotides 809-1277 of trehalase flanked by T7 RNA polymerase recognition sequence. FIG. 3 shows the sequence of SEQ ID NO: 11; the *D. citri* sequences contained in the 5' primer (SEQ ID NO: 12) and 3' primer (SEQ ID NO: 13) are bolded and underlined. The T7 RNA polymerase sequences in these primers are not present in FIG. 3. This amplicon was then cloned into a pCR™2.1-TOPO® plasmid using the TOPO® TA cloning Kit, Cat. No. K4500J10 (Invitrogen, Waltham, Mass.). The plasmid (hereafter named pACP-Tr_3) was then transfected into One Shot TOP 10 competent *E. coli*.

For double-strand RNA synthesis, each of the DNA polynucleotides encoding trehalase (nucleotides 809-1277, SEQ ID NO: 1; nucleotides 168-605, SEQ ID NO: 6; and nucleotides 1157-1886, SEQ ID NO: 11) was synthesized in separate reactions. For this purpose, the plasmid pACP-Tr_1 containing nucleotides 809-1277 of trehalase (SEQ ID NO: 1) flanked by T7 RNA polymerase recognition sequences was combined with the 5' primer (SEQ ID NO: 2) and the 3' primer (SEQ ID NO: 3), DNA polymerase, nucleotides and the appropriated buffer per AmpliTaq Gold® 360 Master Mix Cat. No. 4398881 (Applied Biosystems, Waltham, Mass.) to generate an amplicon containing nucleotides 809-1277 of trehalase flanked by T7 RNA polymerase recognition sequences. The plasmid pACP-Tr_2 containing nucleotides 168-605 of trehalase (SEQ ID NO: 6) flanked by T7 RNA polymerase recognition sequences was combined with the 5' primer (SEQ ID NO: 7) and the 3' primer (SEQ ID NO: 8), DNA polymerase, nucleotides and the appropriated buffer per AmpliTaq Gold® 360 Master Mix Cat. No. 4398881 (Applied Biosystems, Waltham, Mass.) to generate an amplicon containing nucleotides 168-605 of trehalase flanked by T7 RNA polymerase recognition sequences. The plasmid pACP-Tr_3 containing nucleotides 1157-1886 of trehalase (SEQ ID NO: 11) flanked by T7 RNA polymerase recognition sequences was combined with the 5' primer (SEQ ID NO: 12) and the 3' primer (SEQ ID NO: 13), DNA polymerase, nucleotides and the appropriated buffer per AmpliTaq Gold® 360 Master Mix Cat. No. 4398881 (Applied Biosystems, Waltham, Mass.) to generate an amplicon containing nucleotides 1157-1886 of trehalase flanked by T7 RNA polymerase recognition sequences. Each of these amplicons were submitted to electrophoresis to check for presence of a single band of the correct size. Each amplicon was separately purified. Each of the purified amplicons were separately combined with the T7 RNA polymerase, nucleotides, and the appropriate buffer per MEGAscript kit (Life Technologies, Waltham, Mass.) to produce sense and anti-sense single-stranded RNA having the sequences of SEQ ID NOs: 4 and 5 (nucleotides 809-1277of trehalase); the sequence of SEQ ID NOs: 9 and 10 (nucleotides 168-605 of trehalase); and the sequence of SEQ ID NOs: 14 and 15 (nucleotides 1157-1886 of trehalase), respectively. The sense and anti-sense single-stranded RNAs are then allowed to anneal to produce double-stranded RNA. Each set of dsRNAs produced were digested with RNAse A and DNAse to remove single-strand RNA and DNA, respectively, purified and quantified.

A cDNA encoding the maternal protein exuperantia (SEQ ID NO: 16) was synthesized from *D. citri* total RNA extracted using Trizol (Invitrogen, Waltham, Mass.). cDNA was transcribed from 5 μg of total RNA using SuperScript® III First-Strand Synthesis System Cat. No. (Invitrogen, Waltham, Mass.), using random hexamers provided by the manufacturer. The region nucleotides 1-447 of exuperantia (SEQ ID NO: 16) was amplified by PCR by combining the cDNA, the 5' primer (SEQ ID NO: 17) and the 3' primer (SEQ ID NO: 18) with DNA polymerase, nucleotides and the appropriated buffer per AmpliTaq Gold® 360 Master Mix Cat. No. 4398881 (Applied Biosystems, Waltham, Mass.) to generate an amplicon containing nucleotides 1-447 of exuperantia flanked by T7 RNA polymerase recognition sequence. This amplicon was cloned into the pCR™2.1-TOPO® plasmid using the TOPO® TA cloning Kit, Cat. No. K4500J10 (Invitrogen, Waltham, Mass.). The plasmid (hereafter named pACP-Exu_1) is then transfected into One Shot TOP 10 competent *E. coli*. For double-strand RNA synthesis, first DNA polynucleotide encoding nucleotides 1-447 of exuperantia (SEQ ID NO: 16) was synthesized by combining the plasmid p-ACP-Exu_1 containing nucleotides 1-447 of exuperantia (SEQ ID NO: 16) flanked by T7 RNA polymerase recognition sequences, the 5' primer (SEQ ID NO: 17), and the 3' primer (SEQ ID NO: 18), DNA polymerase, nucleotides and the appropriated buffer per AmpliTaq Gold® 360 Master Mix Cat. No. 4398881 (Applied Biosystems, Waltham, Mass.) to produce an amplicon containing nucleotides 1-447 of exuperantia flanked by T7 RNA polymerase recognition sequences. The generated amplicon was submitted to electrophoresis to check for presence of a single band of the correct size, and then the amplicon was purified. The purified amplicon was combined with the T7 RNA polymerase, nucleotides, and the appropriate buffer per MEGAscript kit (Life Technologies, Waltham, Mass.) to produce sense and anti-sense single-stranded RNA having the sequences of SEQ ID NOs: 19 and 20, respectively. The sense and anti-sense single-stranded RNAs are then allowed to anneal to produce double-stranded RNA. The produced dsRNA was digested with RNAse A and DNAse to remove single-strand RNA and DNA, respectively, purified and quantified.

A cDNA encoding nucleotides 3-268 of pterin-4-alpha-carbinolamine dehydratase (PCBD1) (SEQ ID NO: 21) was synthesized from *D. citri* total RNA extracted using Trizol (Invitrogen, Waltham, Mass.). cDNA was transcribed from 5 µg of total RNA using SuperScript® III First-Strand Synthesis System Cat. No. (Invitrogen, Waltham, Mass.), using random hexamers provided by the manufacturer. The region encoding nucleotides 3-268 of PCBD1 (SEQ ID NO: 21) was amplified by PCR combining the cDNA, the 5' primer (SEQ ID NO: 22) and the 3' primer (SEQ ID NO: 23) with DNA polymerase, nucleotides and the appropriated buffer per AmpliTaq Gold® 360 Master Mix Cat. No. 4398881 (Applied Biosystems, Waltham, Mass.) to produce an amplicon containing nucleotides 3-268 of PCBD1 flanked by T7 RNA polymerase recognition sequences. This amplicon was cloned into the pCR™2.1-TOPO® plasmid using the TOPO® TA cloning Kit, Cat. No. K4500J10 (Invitrogen, Waltham, Mass.). The plasmid (hereafter named pACP-Pcd_1) is then transfected into One Shot TOP 10® competent *E. coli*. For double-strand RNA synthesis, a DNA polynucleotide encoding nucleotides 3-268 of PCBD1 (SEQ ID NO: 21) was synthesized by combining the plasmid pACP-Pcbd1_1 containing nucleotides 3-268 of PCBD1 (SEQ ID NO: 21) flanked by T7 RNA polymerase recognition sequences, the 5' primer (SEQ ID NO: 22) and the 3' primer (SEQ ID NO: 23), DNA polymerase, nucleotides and the appropriated buffer per AmpliTaq Gold® 360 Master Mix Cat. No. 4398881 (Applied Biosystems, Waltham, Mass.) to generate an amplicon. This amplicon was submitted to electrophoresis to check for presence of a single band of the correct size and then purified. The purified amplicon encoding nucleotides 3-268 of PCBD1 (SEQ ID NO: 21) flanked by T7 RNA polymerase recognition sequences was combined with the T7 RNA polymerase, nucleotides, and the appropriate buffer per MEGAscript kit (Life Technologies, Waltham, Mass.) to produce sense and anti-sense single-stranded RNA (SEQ NOs: 24 and 25, respectively) which were allowed to anneal to form double-stranded RNA. The dsRNA was digested with RNAse A and DNAse to remove single-strand RNA and DNA, respectively, purified and quantified.

EXAMPLE 2

Psyllid RNAi Feeding Bioassay-cuttings

In general, the RNAi feeding bioassay using plant cuttings has the following protocol. In citrus, the "flush", which are new foliar shoots growth, were collected from potted citrus seedlings grown in a glasshouse to produce small cuttings. The flush are about 7-8 cm long. The plant flush was washed in 0.2% bleach water, for 10 min. Then the base of each stem of each flush was cut at a 45 degree angle while submerged in filtered water. The flush was then placed into a 1.5 mL tube containing 0.5 mL water. A dsRNA solution (100 ng of dsRNA in 300 μL of water) was added to the water in the tube, the tube top was wrapped with plastic or Parafilm™ (Bemis NA, Neenah, Wis.) and placed under artificial lighting to stimulate absorption of the dsRNA solution. After the flush absorbs the entire dsRNA solution (approximately 8 hours), the tube was filled with water using a 26 gauge syringe needle and syringed filtered (0.45 μ). The treated cuttings were then placed in a cage and approximately 15 adult insects of *D. citri* (actual number of insects per cage per experiment ranges from 13 to 18 insects) were added to the cage to feed on the treated cutting. Mortality of adult *D. citri* were scored daily for up to 15 days after start of feeding access period.

Using this RNAi feeding bioassay, dsRNA based on SEQ ID NO: 1 (SEQ ID NOs: 4 and 5, sense and anti-sense strands respectively), SEQ ID NO: 6 (SEQ ID NOs: 9 and 10, sense and anti-sense strands respectively), and SEQ ID NO: 11 (SEQ ID NOs: 14 and 15, sense and anti-sense strands respectively), were evaluated for their capacity to cause mortality on *D. citri*. Treatments were (1) cuttings with dsRNA based on SEQ ID NO: 1; (2) cuttings with dsRNA based on SEQ ID NO: 6; (3) cuttings with dsRNA based on SEQ ID NO: 11; (4) negative control (cuttings that just receive water). Each treatment group were composed of three replicates (a replicate means one cage containing one cutting and approximately fifteen adult *D. citri*).

Insect mortality scored after 15 days of feeding on treated and control cuttings, showed that Treatment #1 (dsRNA based on SEQ ID NO: 1) increased average mortality to 95.92% of the insects among replicates (47 of 49 adult insects). Treatment #2 (dsRNA based on SEQ ID NO: 6) increased average mortality to 86.36% of the insects among replicates (38 of 44 adult insects). Treatment #3 (dsRNA based on SEQ ID NO: 11) increased average mortality to 55.56% of the insects among replicates (25 of 45 adult insects). Treatment #4 (negative control) increased average mortality to 6.67% of the insects among replicates (3 of 45 adult insects).

Using this RNAi feeding bioassay, dsRNA based on SEQ ID NO: 16 (SEQ ID NOs: 19 and 20, sense and anti-sense strands respectively), was evaluated for its capacity to cause mortality on *D. citri*. Treatments were (1) cuttings with dsRNA based on SEQ ID NO: 16; and (2) negative control (cuttings that just received water). Each treatment were composed of three replicates. In this experiment, each cutting, treated with either dsRNA based on SEQ ID NO: 16 or the negative control, was caged with about 12 adult *D. citri* (number of *D. citri* per cage ranged from 11 to 13 insects). Treatment #1 was represented by four replicates, and Treatment #2 was represented by three replicates (a replicate means one cage containing one cutting and about twelve adult *D. citri*).

Insect mortality scored after 15 days of feeding on treated and negative control cuttings, indicated that Treatment #1 increased average mortality to 16.08% of the insects among replicates (8 of 49 adult insects). Treatment #2 induced an average mortality of 3.03% of the insects among replicates (1 of 34 adult insects).

Using this RNAi feeding bioassay, dsRNA based on SEQ ID NO: 21 (SEQ ID NOs: 24 and 25, sense and anti-sense strands respectively), was evaluated for its capacity to cause mortality on *D. citri*. Treatments consisted of (1) cuttings with dsRNA based on SEQ ID NO: 21; (2) negative control (cuttings that just received water). Each treatment were composed of three replicates. In this experiment, each cutting, treated with either dsRNA based on SEQ ID NO: 21 or the negative control, was caged with about 12 adult *D. citri* (number of *D. citri* per cage ranged from 11 to 13 insects). Treatment #1 was represented by four replicates, and Treatment 42 was represented by three replicates (a replicate means one cage containing one cutting and about twelve adult *D. citri*).

Insect mortality scored after 15 days of feeding on dsRNA treated and negative control cuttings, indicated that Treatment #1 induced an average mortality of 4.17% of the insects among replicates (2 of 48 adult insects). Treatment #2 induced an average mortality of 2.08% of the insects among replicates (1 of 48 adult insects)

EXAMPLE 3

Psyllid RNAi Feeding Bioassay—Seedling

Sweet orange seedlings were cultivated in plastic containers (2 gallon pots) containing potting soil and maintained in a glasshouse. Seedlings about 30 cm or 12 inches tall were trimmed, removing all branches, leaving just the seedling trunk. When the seedling produced new growth two weeks post-trimming, 20 adult female *D. citri* were caged on each plant, so they could oviposit eggs for 48 hours. The adults were then removed, and 10 μg of trehalase dsRNA (based on SEQ ID NO: 1) was mixed with 10 mL of water, and the dsRNA solution was poured onto the soil. Seedlings were watered as needed post-treatment. Three sweet orange seedlings were treated with dsRNA based on SEQ ID NO: 1 (treatment #1), and three sweet orange seedlings received just 10 mL of water (treatment #2, negative control). All three seedlings from each treatment group were caged together in a Bug Dorm 2 rearing cage, catalog #1462W (BioQuip, Rancho Dominguez, Calif.). The plants were maintained at 22° C. The development of *D. citri* was monitored over time. For all six seedlings, the eggs hatched, the nymphs developed successfully without any problems, and no mortality occurred (as determined by an absence of dead nymphs observed on the bottom of the cage), thus indicating that the dsRNA based on SEQ ID NO: 1 did not negatively impact nymph survival. About thirty days post-treatment, the nymphs successfully emerge as *D. citri* adults. When *D. citri* adults were approximately 10 days old, they started to die and fall on the bottom of the cage. The total number of dead adults *D. citri* were counted at fourteen days after emergence, post-eclosion. Treatment #1 resulted in death of 100% of *D. citri* adults in this assay (643 dead adult *D. citri* were counted). At the same time, no significant mortality were observed for *D. citri* adults in the negative control cage (Treatment #2).

Life cycle of *D. citri* from egg to adults vary with temperature: at 25° C. eggs hatch in 4 days and nymphs develop to the adult stage over a 13 day period for a total of 17 days from egg to adult (Tsai and Liu, *J. Econ. Entomol.* 93(6):1721-1725 (2000)). Mean development from egg to adult varies from 49.3 days at 15° C. to 14.1 days at 24° C. (Liu and Tsai, *Ann. Appl. Biol.* 137: 201-206 (2000)). At 24° C., adult males live an average of 21 to 25 days, and females live an average of 31 to 32 days (Nava, et al., *Appl. Entomol.* 131:709-715 (2007)). These life parameters show that the conditions of the above experiment did not negatively influence nymph development, and that the mortality of *D. citri* adults that fed on the plants treated with dsRNA based on SEQ ID NO: 1 was not caused by natural causes, because the *D. citri* died when they were fairly young adults (10-14 days old). Thus, dsRNA based on SEQ ID NO: 1 suppressed *D. citri* population by reducing fitness and survival of the adult *D. citri* that developed from nymphs that fed on treated plants. This example demonstrates that dsRNA based SEQ ID NO: 1, nucleotides 809-1277 of trehalase, can suppress ACP population by killing the adult ACPs that feed and/or develop from nymphs on treated plants.

EXAMPLE 4

Genetically Altered Citrus Plants, or Phylogenetically Related Plants, which have Ability to Reduce Fitness and Survival of *D. citri* which Feed on it The generation of transgenic citrus plants that express the dsRNA based on SEQ ID NO: 1 (SEQ ID NOs: 4 and 5, sense and anti-sense strands respectively), is obtained using the protocol described in Oliveira, et al. (2015) *SpringerPlus* 4:264. In vitro-grown etiolated epicotyls segments of 'Hamlin' sweet orange [*Citrus sinensis* (L.) Osbeck.] is used as source of explants. The epicotyl portions of etiolated seedlings is cut transversally into 0.8-1 cm segments and is used for transformation. An *Agrobacterium*-mediated transformation method is used to transform citrus tissue. The plasmid pCACP-Tr_1 is generated by inserting the amplicon correspondent to SEQ ID NO: 1 (SEQ ID NOs: 4 and 5, sense and anti-sense strands respectively), into the pCambia2300. The plasmid is transformed into *A. tumefaciens* EHA 105 (Hood, et al. (1986) *J. Bac.* 168:1291-1301) using freeze-thaw method (Hfgen and Willmitzer (1988) *Nucleic Acids Res.* 16:9877), Epicotyl tissue of 'Hamlin' sweet orange is inoculated for 15 minutes with an overnight culture of *Agrobacterium* diluted to OD 600=0.4 The infected epicotyl tissue is co-cultivated for 3 days on MS basal medium containing 3% sucrose, 1 mg 1-1 BAP, 100 mg 1-1 acetosyringone, 8.0 g 1-1 agar and incubated at an average temperature of 24±1° C. in the dark. After 3 days of cocultivation, the explants is transferred to MS medium containing 300 mg 1-1 timentin, 250 mg 1-1 cefotaxime, and 100 mg 1-1 kanamycin. After 45 days in culture on kanamycin selection media, putatively transformed shoots is transferred to a root-induction medium (RIM), consisting of MS strength medium, 2% sucrose, 0.25% Gelrite, 2.5 mg 1-1 IBA, 0.5 mg 1-1 NAA, and 0.0025 mg 1-1 spermidine. Plants that develop root systems is transferred to sterile soil cones, covered with plastic bags and gradually exposed to ambient humidity in a growth chamber, over a period of 15 days. Acclimated plants is transferred to greenhouse for maturation. To confirm the plant contains the transgene (SEQ ID NO: 1), genomic DNA is extracted using Purelink® Genomic Plant DNA Purification Kit, Cat. Number K1830-01 (Invitrogen, Waltham, Mass.) and is used as a template in a PCR, using the 5' primer (SEQ ID NO: 2) and the 3' primer (SEQ ID NO: 3) with DNA polymerase, nucleotides and the appropriated buffer per AmpliTaq Gold® 360 Master Mix Cat. No. 4398881 (Applied Biosystems, Waltham, Mass.), The PCR amplified product is separated on a 1.2% agarose gel and visualized by ethidium bromide staining.

EXAMPLE 5

RNAi Feeding Bioassay for Potential Off-target Effects in Non-target Beneficial Insects Honey bees (*Apis mellifera*) are beneficial insects to citrus trees, acting as a pollinator. The bees also feeds the nectar and pollen from the plant, and by chance could ingest trehalase dsRNA (based on SEQ ID NO: 1) from a treated citrus tree. To evaluate the absence of harm effects of trehalase dsRNA (based on SEQ ID NO: 1) to a non-target insect, i.e., honey bees, a feeding bioassay was conducted. A frame with mature sealed brood was taken from the colony and held overnight in 33° C. inside the emergence frame box. A group of 30 newly emerged bees were handfed with 5 μL of a 1:1 dsRNA:sucrose solution containing 10 ng of trehalase dsRNA based on SEQ ID NO: 1 (treatment #1). A second group of 30 newly emerged bees were handfed with 5 μL of a 1:1 sucrose solution (treatment #2, negative control water). Bees from each treatment were marked by paint (bees from each treatment were painted with a different color) and placed all together into the same hive. After 10 days, the bees were collected by micro vacuum, and the number of recovered marked bees counted. The percentage of insects in treatment #1 group recovered after 10 days was 73% (22 recovered from 30 treated). The percentage of insects in treatment #2 group recovered after 10 days was 70% (21 recovered from 30 treated). Additionally, the recovered individual honey bees from each treatment group were analyzed for any significant changes on the levels of some mRNAs using the RT-qPCR protocol set forth in Evans (2006) (*J. Invert. Path.* 93:135-139). The mRNA levels for the following genes were analyzed: vitellogenin (NCBI Reference Sequence: NM_001011578.1), eater (also called nimrodC1) (NCBI Reference Sequence: XM_006561053.1), hymenoptaecin (NCBI Reference Sequence: NM_001011615.1) and arginine kinase (NCBI Reference Sequence: NM_001011603). The ribosomal protein 5 gene (NCBI Reference Sequence: XM_006567834.1) was used as a reference gene. Primer pairs were designed for each of these genes using Printer 3 (bioinfo.ut.ee/primer3-0.4.0/primer3/). Comparative analysis of the mRNA levels of each gene from individuals honey bees from treatment #1 and treatment #2 were not significantly different by one-way ANOVA analysis. Thus, dsRNA based SEQ ID NO: 1, nucleotides 809-1277 of trehalase, did not produce a harmful effect when ingested by honey bees.

The foregoing detailed description and certain representative embodiments and details of the invention have been presented for purposes of illustration and description of the invention. It is not intended to be exhaustive or to limit the invention to the precise forms disclosed. It will be apparent to practitioners skilled in the art that modifications and variations may be made therein without departing from the scope of the invention. All references cited herein are incorporated by reference.

We, the inventors, claim:

1. A dsRNA comprising a sense region consisting a sequence of at least twenty-one contiguous ribonucleotides equivalent to *D. citri* trehalase cDNA of SEQ ID NO: 26 and an anti-sense region complementary to said sense region, and wherein the sequence of the anti-sense region is at least 95% identical to the complement of said sense region; and wherein *D. citri* are killed upon ingestion or adsorption of said dsRNA.

2. The dsRNA of claim 1 wherein said dsRNA comprises a sequence selected from the group consisting of between 21 nt and 469 nt of SEQ ID NO: 4 or a sequence at least 99% identical thereof, between 21 nt and 438 nt of SEQ ID NO: 9 or a sequence at least 99% identical thereof, and between 21 nt and 730 nt of SEQ ID NO: 14 or a sequence at least 99% identical thereof.

3. A dsRNA solution comprising an agriculturally acceptable carrier and said dsRNA of claim 1.

4. The dsRNA solution of claim 3, wherein said agriculturally acceptable carrier is selected from the group consisting of water, surfactant, liposome, lipid, protein, peptide, nanotube, chitin, inactivated microorganism, and a combination thereof.

5. The dsRNA solution of claim 3, wherein said dsRNA solution further comprises a compound that prevent dsRNA degradation, a translaminar chemical, a mineral, a clay, a fertilizer, a sugar, or a combination thereof.

6. A method of reducing *Diaphorina citri* infestation on a treated plant compared to the *D. citri* infestation on an untreated plant, said method comprising administering a dsRNA solution having insecticidal activity against said *D. citri* to an untreated plant in an amount effective to kill said *D. citri* to generate a treated plant, and allowing said *D. citri* to ingest or absorb said dsRNA solution, wherein said dsRNA solution comprises an agriculturally acceptable carrier and said dsRNA of claim 1, and wherein said dsRNA kills said *D. citri* that ingest or absorb said dsRNA solution and thereby reduces said *D. citri* infestation on said treated plant compared to said *D. citri* infestation on said untreated plant.

7. The method of claim 6, wherein said dsRNA comprises a sequence selected from the group consisting of between 21 nt and 469 nt of SEQ ID NO: 4 or a sequence at least 99% identical thereof, and between 21 nt and 438 nt of SEQ ID NO: 9 or a sequence at least 99% identical thereof, between 21 nt and 730 nt of SEQ ID NO: 14 or a sequence at least 99% identical thereof.

8. The method of claim 6, wherein said agriculturally acceptable carrier is selected from the group consisting of water, surfactant, liposome, lipid, protein, peptide, nanotube, chitin, inactivated microorganism, and a combination thereof.

9. The method of claim 6, wherein said dsRNA solution further comprises a compound that prevent dsRNA degradation, a translaminar chemical, a mineral, a clay, a fertilizer, a sugar, or a combination thereof.

10. The method of claim 6, wherein said administering step comprises spraying said dsRNA solution onto said untreated plant to generate said treated plant.

11. The method of claim 6, wherein said administering step comprises applying said dsRNA solution to soil surrounding said untreated plant to allow for roots of said untreated plant to absorb said dsRNA and generating said treated plant.

12. The method of claim 6, wherein said administering step comprising applying said dsRNA solution to one or more roots of said untreated plant to generate said treated plant.

13. A method for reducing fitness or survival of *D. citri* comprising introducing said dsRNA of claim 1 into a wild-type plant upon which said *D. citri* feeds, thereby producing an altered plant containing said dsRNA, and allowing *D. citri* to feed on said altered plant containing said dsRNA, wherein said dsRNA reduces said fitness or survival of said *D. citri* that ingest said dsRNA.

14. The method of claim 13, wherein said dsRNA comprises a sequence selected from the group consisting of between 21 nt and 469 nt of SEQ ID NO: 4 or a sequence at least 99% identical thereof, between 21 nt and 438 nt of SEQ ID NO: 9 or a sequence at least 99% identical thereof, and between 21 nt and 730 nt of SEQ ID NO: 14 or a sequence at least 99% identical thereof.

15. The method of claim 14, wherein said introducing said dsRNA into said wild-type plant comprises spraying a dsRNA solution comprising said dsRNA onto said wild-type plant.

16. The method of claim 14, wherein said introducing said dsRNA into said wild-type plant comprises applying a dsRNA solution comprising said dsRNA to roots of said wild-type plant.

17. The method of claim 14, wherein said introducing said dsRNA into said wild-type plant comprises applying a dsRNA solution comprising said dsRNA to soil around said wild-type plant whereby roots of said wild-type plant absorb said dsRNA.

18. The method of claim 13, wherein said introducing said dsRNA into a wild-type plant comprises transforming a wild-type plant cell with an expression vector encoding said dsRNA to produce an altered plant cell; selecting said altered plant cell that produces said dsRNA; and inducing said altered plant cell that produces said dsRNA to grow into said altered plant that produces said dsRNA; wherein said expression vector comprises at least one heterologous promoter operably linked a polynucleotide encoding said dsRNA comprising a sense region and an anti-sense region, wherein said dsRNA comprises a sequence selected from the group consisting of between 21 nt and 469 nt of SEQ ID NO: 4 or a sequence at least 99% identical thereof, between 21 nt and 438 nt of SEQ ID NO: 9 or a sequence at least 99% identical thereof, between 21 nt and 730 nt of SEQ ID NO: 14 or a sequence at least 99% identical thereof, and between 21 nt and 1908 nt of the RNA equivalent of SEQ ID NO: 26 or a sequence at least 95% identical thereof.

19. The method of claim 18 wherein said expression vector comprises one promoter which controls transcription of said sense region and said anti-sense region.

20. The method of claim 18, wherein said expression vector comprises a first promoter which controls transcription of said sense region and a second promoter which controls transcription of said anti-sense region.

21. A method of reducing transmission by *D. citri* of a disease-causing microorganism from a treated plant to an untreated plant, said method comprising applying a dsRNA solution to a wild-type plant to produce said treated plant, and allowing *D. citri* to feed on said treated plant, wherein said dsRNA solution comprises an agriculturally acceptable carrier and said dsRNA of claim 1, and wherein said dsRNA kills said *D. citri* that ingests or absorbs said dsRNA, wherein said dead *D. citri* are unable to transmit said microorganism to an untreated plant.

22. The method of claim 21 wherein said dsRNA comprises a sequence selected from the group consisting of between 21 nt and 469 nt of SEQ ID NO: 4 or a sequence at least 99% identical thereof, between 21 nt and 438 nt of SEQ ID NO: 9 or a sequence at least 99% identical thereof, between 21 nt and 730 nt of SEQ ID NO: 14 or a sequence at least 99% identical thereof, and between 21 nt and 1908 nt of the RNA equivalent of SEQ ID NO: 26 or a sequence at least 95% identical thereof.

23. The method of claim 21, wherein said applying said dsRNA solution to said wild-type plant comprises spraying said dsRNA solution onto said wild-type plant.

24. The method of claim 21, wherein said applying said dsRNA solution to said wild-type plant comprises applying said dsRNA solution to roots of said wild-type plant.

25. The method of claim 21, wherein said applying said dsRNA solution to said wild-type plant comprises applying said dsRNA solution to soil around said wild-type plant whereby roots of said wild-type plant absorb said *D. citri* trehalase dsRNA.

26. A genetically altered plant and parts thereof comprising an expression vector comprising a first promoter operably linked to a *D. citri* trehalase sense polynucleotide and a second promoter operably linked to a *D. citri* trehalase anti-sense polynucleotide, wherein said *D. citri* trehalase sense polynucleotide is the reverse complement of said *D. citri* trehalase anti-sense polyncleotide; wherein said *D. citri* trehalase sense polynucleotide comprises a sequence selected from the group consisting of between 21 nt and 469 nt of SEQ ID NO:1 or a sequence at least 99% identical thereof, between 21 nt and 438 nt of SEQ ID NO: 6 or a sequence at least 99% identical thereof, between 21 nt and 730 nt of SEQ ID NO: 11 or a sequence at least 99% identical thereof, and between 21 nt and 1908 nt of SEQ ID NO: 26 or a sequence at least 95% identical thereof; and wherein *D. citri* are killed upon ingestion or adsorption of said dsRNA.

27. The genetically altered plant and parts thereof of claim 26 wherein said first promoter and said second promoter are the same promoters.

28. The genetically altered plant and parts thereof of claim 26 wherein said first promoter and said second promoter are different promoters.

29. A genetically altered plant and parts thereof comprising an expression vector comprising a promoter operably linked to a polynucleotide comprising a *D. citri* trehalase sense region and a *D. citri* trehalase anti-sense region, wherein said *D. citri* trehalase anti-sense region is the reverse complement of said *D. citri* trehalase sense region; and wherein said *D. citri* trehalase sense region comprises a sequence selected from the group consisting of between 21 nt and 469 nt of SEQ ID NO: 4 or a sequence at least 99% identical thereof, between 21 nt and 438 nt of SEQ ID NO: 9 or a sequence at least 99% identical thereof, between 21 nt and 730 nt of SEQ ID NO: 14 or a sequence at least 99% identical thereof, and between 21 nt and 1908 nt of SEQ ID NO: 26 or a sequence at least 95% identical thereof; wherein said *D. citri* trehalase sense region and a *D. citri* trehalase anti-sense region form a dsRNA; and wherein *D. citri* are killed upon ingestion or adsorption of said dsRNA.

30. A method for making a genetically altered plant that produces a *D. citri* trehalase dsRNA, the method comprising transforming a wild-type plant cell with an expression vector that encodes *D. citri* trehalase dsRNA to generate a genetically altered plant cell, selecting for a genetically altered plant cell that produces said *D. citri* trehalase dsRNA to generate a selected genetically altered plant cell, and growing said selected genetically altered plant cell to produce said genetically altered plant that produces said *D. citri* trehalase dsRNA; wherein said *D. citri* trehalase dsRNA comprises a sense region and an anti-sense region wherein said sense region is the reverse complement of said anti-sense region, and wherein said sense region is encoded by a sequence selected from the group consisting of between 21 nt and 469 nt of SEQ ID NO: 1 or a sequence at least 99% identical thereof, between 21 nt and 438 nt of SEQ ID NO: 6 or a sequence at least 99% identical thereof, between 21 nt and 730 nt of SEQ ID NO: 11 or a sequence at least 99 % identical thereof, and between 21 nt and 1908 nt of SEQ ID NO: 26 or a sequence at least 95% identical thereof; and wherein *D. citri* are killed upon ingestion or adsorption of said dsRNA.

31. The method of claim 30, wherein said expression vector comprises a promoter operably linked to a polynucleotide encoding said sense region and said anti-sense region.

32. The method of claim 30, wherein said expression vector comprises a first promoter operably linked to a polynucleotide encoding said sense region and a second promoter operably linked to a polynucleotide encoding said anti-sense region.

33. A genetically altered plant that produces *D. citri* trehalase dsRNA produced by the method comprising (a) transforming a wild-type plant cell with an expression vector that encodes *D. citri* trehalase dsRNA to generate a genetically altered plant cell, (b) selecting for a genetically altered plant cell that produces said *D. citri* trehalase dsRNA to generate a selected genetically altered plant cell, and (c) growing said selected genetically altered plant cell to produce said genetically altered plant that produces said *D. citri* trehalase dsRNA; wherein said *D. citri* trehalase dsRNA comprises a sense region and an anti-sense region wherein said sense region is the reverse complement of said anti-sense region, and wherein said sense region is encoded by a sequence selected from the group consisting of between 21 nt and 469 nt of SEQ ID NO: 1 or a sequence at least 99% identical thereof, between 21 nt and 438 nt of SEQ ID NO: 6 or a sequence at least 99% identical thereof, between 21 nt and 730 nt of SEQ ID NO: 11 or a sequence at least 99% identical thereof, and between 21 nt and 1908 nt of SEQ ID NO: 26 or a sequence at least 95% identical thereof and wherein D. citri are killed upon ingestion or adsorption of said dsRNA.

34. A genetically altered plant cell of said genetically altered plant of claim 33.

35. The method of claim 13 wherein said introducing dsRNA of claim 1 into a wild-type plant comprising infecting said wild-type plant with a recombinant plant virus to form said altered plant, wherein said recombinant plant virus comprises a heterologous polynucleotide encoding said dsRNA, and wherein said recombinant virus produces said dsRNA while replicating in said altered plant.

36. The method of claim 35, wherein when said recombinant plant virus is a DNA virus, said heterologous polynucleotide has a sequence selected from the group consisting of between 21 nt and 469 nt of SEQ ID NO: 1 or a sequence at least 99% identical thereof, between 21 nt and 438 nt of SEQ ID NO: 6 or a sequence at least 99% identical thereof, between 21 nt and 730 nt of SEQ ID NO: 11 or a sequence at least 99% identical thereof, and between 21 nt and 1908 nt of SEQ ID NO: 26 or a sequence at least 95% identical thereof.

37. The method of claim 35, wherein when said recombinant plant virus is a RNA virus, said heterologous polynucleotide has a sequence selected from the group consisting of between 21 nt and 469 nt of SEQ ID NO: 4 or a sequence at least 99% identical thereof, between 21 nt and 438 nt of SEQ ID NO: 9 or a sequence at least 99% identical thereof, between 21 nt and 730 nt of SEQ ID NO: 14 or a sequence at least 99% identical thereof, the RNA equivalent of between 21 nt and 1908 nt of SEQ ID NO: 26 or a sequence at least 95% identical thereof, and the reverse complement thereof.

38. The method of claim 35, wherein when said recombinant plant virus is a RNA virus, said heterologous polynucleotide comprises a sense region, an anti-sense region and optionally, a linker region, wherein said anti-sense region is the reverse complement of said sense region, and wherein said sense region has a sequence selected from the group consisting of between 21 nt and 469 nt of SEQ ID NO: 4 or a sequence at least 99% identical thereof, between 21 nt and 438 nt of SEQ ID NO: 9 or a sequence at least 99% identical thereof, between 21 nt and 730 nt of SEQ ID NO: 14 or a sequence at least 99% identical thereof, and between 21 nt and 1908 nt of the RNA equivalent of SEQ ID NO: 26 or a sequence at least 95% identical thereof.

* * * * *